(12) United States Patent
Li et al.

(10) Patent No.: US 7,915,482 B2
(45) Date of Patent: Mar. 29, 2011

(54) ANTHER SPECIFIC PROMOTERS AND USES THEREOF

(75) Inventors: Song Li, Bulleen (AU); Roger Parish, Warrandyte (AU)

(73) Assignee: Grains Research And Development Corporation, Barton (AU)

(*) Notice: Subject to any disclaimer, the term of this patent is extended or adjusted under 35 U.S.C. 154(b) by 398 days.

(21) Appl. No.: 11/629,827

(22) PCT Filed: Jun. 15, 2005

(86) PCT No.: PCT/AU2005/000853
§ 371 (c)(1),
(2), (4) Date: Mar. 7, 2008

(87) PCT Pub. No.: WO2005/123920
PCT Pub. Date: Dec. 29, 2005

(65) Prior Publication Data
US 2009/0019598 A1    Jan. 15, 2009

(30) Foreign Application Priority Data
Jun. 15, 2004  (AU) ................ 2004903245

(51) Int. Cl.
*A01H 1/00* (2006.01)
*C12N 15/82* (2006.01)
*C12N 15/87* (2006.01)
*C07H 21/04* (2006.01)

(52) U.S. Cl. .................. 800/287; 800/279; 536/24.1

(58) Field of Classification Search .............. None
See application file for complete search history.

(56) References Cited

U.S. PATENT DOCUMENTS

| 5,487,991 | A | 1/1996 | Vandekerckhove et al. ................. 435/172.3 |
| 5,530,194 | A | 6/1996 | Knauf et al. ............... 800/205 |
| 5,589,583 | A | 12/1996 | Klee et al. ................. 536/24.1 |
| 5,589,615 | A | 12/1996 | De Clercq et al. ......... 800/205 |
| 5,608,149 | A | 3/1997 | Barry et al. ................ 800/205 |
| 5,677,474 | A | 10/1997 | Rogers ..................... 800/205 |
| 5,723,751 | A | 3/1998 | Chua ......................... 800/205 |
| 5,925,808 | A * | 7/1999 | Oliver et al. ............. 800/298 |
| 7,132,292 | B2 * | 11/2006 | Komatsu et al. ........... 435/468 |

OTHER PUBLICATIONS

Oommenn et al 1994, The Plant Cell 6:1789-1803.*
Kim et al. 1994, Plant Molecular Biology 24: 105-117.*
Fourgoux-Nicol et al. 1999, Plant Molecular Biology 40 :857-872.*
Nakamura et al. 2000, Genbank Accession No. AB015475.*
Alignment of SEQ ID No. 1 and AB015475.*
Altschul et al., "Gapped BLAST and PSI-BLAST: A New Generation of Protein Database Search Programs," *Nucleic Acids Res.* 25: 3389-3402, 1997.
Genbank database (accession No. AB015475).
GenPept abstract accession No. AAM18178, Mar. 14, 2002, Seul and Hong.
Goldberg et al., "Anther Development: Basic Principles and Practical Applications," *The Plant Cell*, 5: 1217-1223, 1993.
Klimyuk et al., "Alkali treatment for rapid preparation of plant material for reliable PCR analysis," *Plant Journal* 3:493-494, 1993.

* cited by examiner

*Primary Examiner* — Li Zheng
(74) *Attorney, Agent, or Firm* — Ballard Spahr LLP

(57) ABSTRACT

The present invention provides an expression cassette comprising a functional anther specific promoter nucleic acid molecule, homologous to the Ta39 promoter of tobacco, as well as functional homologues, orthologues and fragments of said functional anther specific promoter nucleic acid molecule. Also contemplated, are recombinant plasmids, plant cells and cell lines, transgenic plants and propagating material comprising the functional anther specific promoter nucleic acid molecule.

20 Claims, 13 Drawing Sheets

Identities = 23/76 (30%), Positives = 31/76 (40%), Gaps = 10/76 (13%)

```
IHVLALLLLIFASTKIHHAQGKSITGPCVVACSK--KTIACVVRCRFATDKCSQDCAIDSIHCVSSCLLQNSSSPP
+VL + LLI +S I      S G C V CSK   +   C+  C   +KC+           CV S   N    P
VKVLIISLLITSSLFILSTADSSCGGKCNVRCSKAGRQDRGIKYCNICCEKCN--------YCVPSGTYGNKDECP
```

A.

```
                   At39gene-5' primer
ATG AAA TTC CCG GCT GTA AAA GTT CTT ATT ATC TCT CTT CTC
 M   K   F   P   A   V   K   V   L   I   I   S   L   L
              At39codereq primer
ATC ACA TCT TCT TTG TTC ATA CTC TCA ACC GCG GAT TCG Tgt
 I   T   S   S   L   F   I   L   S   T   A   D   S   S
aag tat aca caa tgc att ttc tta ttt tag ata ctt ttc tca tta gaa att tag ctt tct
taa taa aat tgt att gtg atg atg gat taa tta gCA CCA TGC GGA GGA AAA
                                                 P   C   G   G   K
TGC AAC GTG AGA TGT TCA AAG GCA GGA AGA CAA GAT AGG
 C   N   V   R   C   S   K   A   G   R   Q   D   R
TGT CTC AAG TAT TGT AAT ATA TGT TGC GAG AAG TGT AAC
 C   L   K   Y   C   N   I   C   C   E   K   C   N
                          At39gene-3' primer
TAT TGT GTT CCT TCA GGC ACT TAT GGA AAC AAA GAT GAA
 Y   C   V   P   S   G   T   Y   G   N   K   D   E
TGC CCT TGT TAC CGC GAT ATG AAG AAC TGC AAA GGC ACG
 C   P   C   Y   R   D   M   K   N   S   K   G   T
TTC AAA TGT CCT TGA
 S   K   C   P   *
```

B.

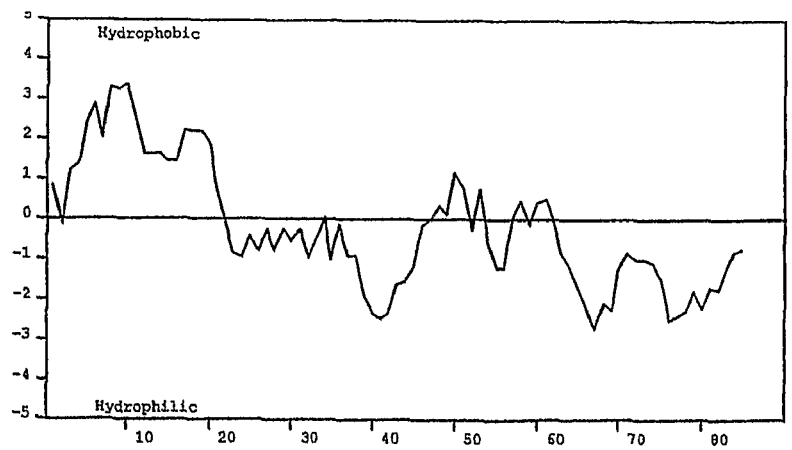

FIGURE 4

```
GCACAAGCTT GCTTATAAGC TACTCTTTGC CAACAAATTC GCAACAATGA TTTCTAGAAC
TATAATCAGT TGATGGGGGA AGAAAATGTT GAAAGTTGTA CAATGAATCA AGTTAAAGTT
AAAATACTTT TTTCCCGATT CTCTGCAGGT TACATATATG TGTATATACA CAGTATGTGA
ATGATCAAAA AGAAGATTTA ATATATCTAA GCATGCAGAC AAAAACCTAT TGCTAAAAAG
ATTTCTAAGA ACCGGAGACC GTTTACCAAA CAAATATGA AGTTGAATTC ATCCCATTTG
TCACTCGATT AGACAAGATT CGTCGAACGA AGATATCTAT TAACGATCTA CTAACTTTAG
TTAAATCGTG ACAAAACACA CATCATTCAT ATTTGATAGT GAATAAGTCG GTGGTCCATC
GTTTTAACTT TGATTGATAT CCTTAAAATT GATGCATAGC TTTAAACAAC CAATACTTTC
TTATGGATTG TTTTTCTTCC AACTTCTCTA AGGGTTTTAT TTTAGAAAAT TGATTATAAG
TATTaaatga AATCTAAGAG AAAAAAAAAA AAAAAAGAG GAGAAAGATG TAGAAGTTCC
CATGCCTTTA GATTCGGATT ACGTGTGTCA CTCTTTTTAT AGCTTTAACG CGATGGTCGC
TCAACGTGAA CGACATTGTC CCACTAAGAA AATAATGAT CATTTCATGT GTATTTTTTC
TTTATCAAAT TTTTAAATta tatataCATA TCTAACTTTG ATAACAACAA CAAGAATCTG
TAATACAATT ATACAACGGC ACGCAAACAG CAGAATTAGT AGATATTCTT TAAAGCAAAT
TTACCATATT TGTAACATTT CTATTAGTAT GATATGATAC AAAAGTTTGG AACATGATTT
GATAGAAGCT AACGTCAATT CCATTTCTTT AATAAATGGT AAAAGGTATA TAAACAGAGT
ATTAGTCCTC AAAAACATTG TAAACATATT GTTTTAAAAC AATTTACCAG TATATATTGA
CAATAGTTTA ACTGAATTGA CGTGCAAGTC AATATTATTA CCTTATTAGG GGGCGTTATT
GGTTCTTAAT TTACAAGGAA TTTAGATGAT TTCAATCACA TTCTATAAAG TATTTTAAAG
TATTGTTAGA GAGTTTTTTA TAATCTTGTT GATTAGTTTT TCATAATTTT GTAAAGTTTT
TCAAACAATC TCTCTATTTT AATAATACTT TTCATGACTT TCCATGACTT TATTTTGTGA
AGAAAAATGT AAAAAGTCAT GAACCAATAA CATAATAATT GAAATCATTA ACAATGAGAA
ATTTTTTTGT TTTAATTGAA TAACACAAAA CTTTTAATGA CTTGAGTATG AATCCAATAA
CCCAAAATTT ATGCAGATTT TAGAATACTT CTTATAAATC TtaaatgaAT AACACAAAAC
TTTAACATAC TTTtaacaaa TCTTGATTGA ATAACAACAG ATTCTACATG ACATTTTAAA
TCACTAAAAC TCTTTTGAAA TCATAAACCA ATAACAACCC CTTAGTTTTT tactatttGA
ATTCtgacgT ACTTTTTTAT TAGTTGAATT TCTATAAATG AGAAAACATT AATTATTTCT
TAATCTTTGA ACTTAAGCCc cacaaaaaTC TTATAAATTG GGACAGATGG ACTAGATAAC
AAGCGTTTCA CCTACTCCAA AATTTCCCTA TAAGTAACTC TTTTTGTAAC CTCCTTTTCT
TCCCAAACCA TCACTCCTTT TGCATTGTGT GAAACCTTCG AGTTTTCTCT TCATCTTCTC
AAAGTAACAA ACTTTCTCCA AACAGATTAT TATTAAAACA ATCTCATCAA GAACTACGAT
G
```

Figure 5

```
                90         100        110        120        130        140        150        160
                 |          |          |          |          |          |          |     XbaI |
TTGATCTTTTAATTCGNGATTGCACAAGCTTGCTTATAAGCTACTCTTTGCCAACAAACTCGCAACAATGATTTCTAGAA
                            GCACAAGCTTGCTTATAAGCTACTCTTTGCCAACAAATTCGCAACAATGATTTCTAGAA
                             |          |          |          |          |
                             10         20         30         40         50

170        180        190        200        210        220        230        240
          |          |          |          |          |          |          |          |
CTATACTCAGTTGATGGGGGAAGAAAATGTTGAAAGTTGTACAATGAATCAAGTTAAAGTTAAAATACTTTTTTTCCCGAT
CTATAATCAGTTGATGGGGGAAGAAAATGTTGAAAGTTGTACAATGAATCAAGTTAAAGTTAAAATACTTTTTTTCCCGAT
 |          |          |          |          |          |          |          |
 60         70         80         90         100        110        120        130

250        260        270        280        290        300        310        320
          |          |          |          |          |          |          |  SphI    |
TCTCTGCAGGTTACATATATGTGTATATACACAGTATGTGAATGATCAAAAAGAAGATTTAATATATCTAAGCATGCAGA
TCTCTGCAGGTTACATATATGTGTATATACACAGTATGTGAATGATCAAAAAGAAGATTTAATATATCTAAGCATGCAGA
 |          |          |          |          |          |          |          |
 140        150        160        170        180        190        200        210

330        340        350        360        370        380        390        400
          |          |          |          |          |          |          |          |
CAAAAACCTATTGCTAAAAAGATTTCTAAGAACCGGAGACCGTTTACCAAACAAAATATGAAGTTGAATTCATCCCATTT
CAAAAACCTATTGCTAAAAAGATTTCTAAGAACCGGAGACCGTTTACCAAACAAAATATGAAGTTGAATTCATCCCATTT
 |          |          |          |          |          |          |          |
 220        230        240        250        260        270        280        290

410        420        430        440        450        460        470        480
          |          |          |          |          |          |          |          |
GTCACTCGATTAGACAAGATTCGTCGAACGAAGATATCTATTAACGATCTACTAACTTTAGTTAAATCGTGACAAAACAC
GTCACTCGATTAGACAAGATTCGTCGAACGAAGATATCTATTAACGATCTACTAACTTTAGTTAAATCGTGACAAAACAC
 |          |          |          |          |          |          |          |
 300        310        320        330        340        350        360        370

490        500        510        520        530        540        550        560
          |          |          |          |          |          |          |          |
AAATCATTCATATTTGATAGTGAATAAGTCGGTGGNCCATCGTTTTAACTTTGATTGATATCCTTAAAATTGATGCATAG
                     570        580        590        600        610        620        630        640
                      |          |          |          |          |          |          |          |
CTTTAAACAACCAATACTTTCTTATGGATTGNTTTTCTTCCAACTTCTCTAAGGGTTTTATTTTAGAAAATTGATTATAA
CTTTAAACAACCAATACTTTCTTATGGATTGTTTTTCTTCCAACTTCTCTAAGGGTTTTATTTTAGAAAATTGATTATAA
 |          |          |          |          |          |          |
 460        470        480        490        500        510        520        530

650        660        670        680        690        700        710        720
          |          |          |          |          |          |          |          |
GTATTAAATGAAATCTAANAGAAAAAAAAAAAAAAAGAGGAGAAAGATGTAGAANTTCCCATGCCTTAAGATTCCGGA
GTATTAAATGAAATCTAAGAGAAAAAAAAAAAAAAGAGGAGAAAGATGTAGAAGTTCCCATGCCTTTAGATTCGGA
 |          |          |          |          |          |          |
 540        550        560        570        580        590        600        610

730        740        750        760        770        780
          |          |          |          |          |          |
TTACGTGTGTCACTCTTTTTATAGCTTTAACGCGATGGTCCGTCAACGTGAACCGACNC
TTACGTGTGTCACTCTTTTTATAGCTTTAACGCGATGGTCCGCTCAACGTGAACCGACATTGTCCCACTAAGAAAATAATG
 |          |          |          |          |          |          |          |
 620        630        640        650        660        670        680        690
```

FIGURE 9

```
        930       940       950       960       970       980       990       1000
         |         |         |         |         |         |         |         |
CTTTTGCATTGTGTGAAACCTTCGAGTTTTCTCTTCATCTTCTCAAAGTAACAAACTTTCTCCAAACAGATTATTATTAA
**********************************************************************
CTTTTGCATTGTGTGAAACCTTCGAGTTTTCTCTTCATCTTCTCAAAGTAACAAACTTTCTCCAAACAGATTATTATTAA
 |         |         |         |         |         |         |         |
1760      1770      1780      1790      1800      1810      1820      1830

1010      1020      1030      1040      1050      1060      1070      1080
         |         |         |         |         |         |         |         |
AACAATCTCATGAAGAACTACGATGAAATTCCCGGCTGTAAAAGTTCGGATCCCCGGGTACGGTCAGTCCCTTATGTTAC
************************       *****              *************
AACAATCTCATCAAGAACTACGATGTTTAAGGGCCGACATTTTCAAGGGATC---------------CCCTTATGTTAC
 |         |         |         |         |                         |
1840      1850      1860      1870      1880                       1890

1090      1100      1110      1120      1130      1140
         |         |         |         |         |         |
GTCCTGTAGAAACCCCAACCGGGAAATCAAAAAANAGACGGCGGGGGCATAANGGGGGAA
*********************  ** *****  *                *
GTCCTGTAGAAACCCCAACCCGTGAAATCAAAAAACTCGACGGCCTGTGGGCATTCAGTCTGGATCGCGAAAACTGTGGA
 |         |         |         |         |         |         |         |
1900      1910      1920      1930      1940      1950      1960      1970
```

FIGURE 11

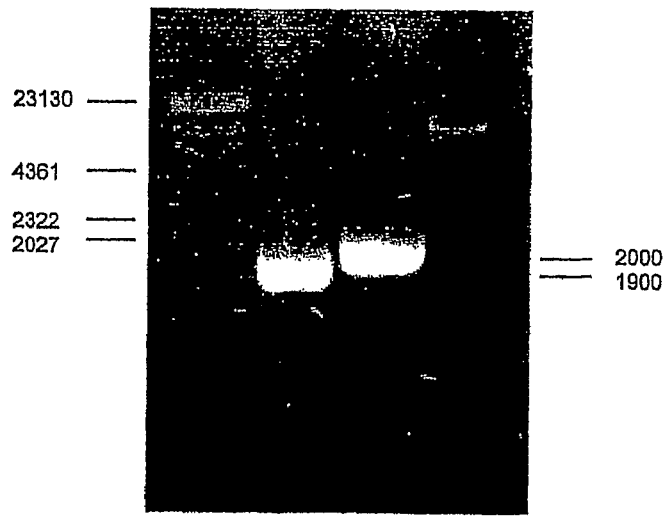

FIGURE 12

A.
B.
FIGURE 14

ANTHER SPECIFIC PROMOTERS AND USES THEREOF

CROSS REFERENCE TO RELATED APPLICATIONS

The present application claims priority to Australian Patent Application No. 2004903245, filed 15 Jun. 2004, which application is incorporated herein fully by this reference.

The present invention relates to anther specific promoters and their use in the production of transgenic plants.

BACKGROUND OF THE INVENTION

The isolation and characterisation of tissue-specific genes allows the analysis of tissue development and the identification of regulatory elements.

An anther-specific promoter is required to direct expression of heterogenous DNA to the anthers and/or pollen, for use, for example in the development of a male sterility system. A number of regulatory sequences from the promoter region of anther or pollen-specific genes have been identified using promoter deletion analysis. Sequence similarities among tissue specific promoters are restricted to short sequence motifs. Promoters may share a similar sequence but are also influenced by upstream regulatory elements that influence expression levels.

The tobacco TA39 gene is expressed in the anther tissue in tobacco (Goldberg et al., (1993) Plant Cell 5: 1217-1229). Unreported studies by the inventors found that TA39 promoter is active only in anthers of Arabidopsis and canola.

It is an aim of the present invention to provide an alternative to the TA39 promoter and to use this anther specific promoter in the production of transgenic plants engineered to have desirable characteristic. It is a further aim of the present invention to provide an anther specific promoter for use in *Arabidopsis*, wheat, Canola and other crops. The invention is particularly important in relation to legumes, crop, cereal and native grasses, fruiting plants, and flowering plants as it provides means for increasing yield.

SUMMARY OF THE INVENTION

Accordingly, in a first aspect, the present invention provides an isolated anther specific promoter nucleic acid molecule comprising:
(a) a nucleotide sequence shown as SEQ ID NO: 1;
(b) a nucleotide sequence that is the promoter of a gene encoding a polypeptide shown as SEQ ID NO: 2;
(c) a homologue or orthologue of a nucleotide sequence of (a) and having at least 50% sequence identity with the nucleotide sequence of (a);
(d) a homologue or orthologue of the nucleotide sequence of (b) and having at least 50% sequence identity with the nucleotide sequence encoding the polypeptide shown as SEQ ID NO: 2;
(e) a nucleotide sequence complementary to the nucleotide sequence of (a), (b), (c) or (d); and/or
(f) a nucleotide sequence capable of hybridising to a nucleotide sequence of (a), (b), (c) or (d) under conditions of high stringency.

In a second aspect the invention provides an anther specific promoter nucleic acid molecule comprising:
(a) a fragment of a nucleotide sequence of the first aspect; and/or
(b) a derivative of a nucleotide sequence of the first aspect, wherein the fragment or derivative is capable of directing expression of a heterologous nucleic acid to which it is operably linked to anther and/or pollen tissue of a plant transformed with the nucleic acid molecule.

In a third aspect the invention provides an expression cassette comprising an anther specific promoter nucleic acid molecule according to the first or second aspects of the invention and a site for inserting a heterologous nucleic acid molecule, such that the heterologous nucleic acid is operably linked to the promoter and is specifically expressed in anther and/or pollen tissue of a plant transformed with the nucleic acid molecule.

In a fourth aspect the invention provides a recombinant plasmid comprising an anther specific promoter nucleic acid molecule according to the first or second aspects of the invention and a heterologous nucleic acid operably linked to the promoter.

In a fifth aspect the invention provides a plant cell or cell line transformed with the nucleic acid molecules according to the first or second aspects of the invention, the expression cassette according to the third aspect of the invention or recombinant plasmid according to the fourth aspect of the invention.

In a sixth aspect the invention provides a transgenic plant generated from the transformed cell according to the fifth aspect of the invention.

In a seventh aspect the invention provides a method for introducing into a plant a heterologous nucleic acid molecule which is to be specifically expressed in anthers and/or pollen, the method comprising the steps of:
(a) transforming a plant cell with the nucleic acid molecules according to the first or second aspects of the invention, the expression cassette according to the third aspect of the invention or the recombinant plasmid according to the fourth aspect of the invention; and
(b) generating a plant from the transformed plant cell.

In an eighth aspect the invention provides a method of specifically expressing a heterologous nucleic acid molecule in anther and/or pollen of a plant, the method comprising the steps of:
(a) transforming a plant cell with the nucleic acid molecules according to the first or second aspects of the invention, the expression cassette according to the third aspect of the invention or the recombinant plasmid according to the fourth aspect of the invention; and
(b) generating the plant from the plant cell.

In a ninth aspect the invention provides the use of the nucleic acid molecules according to the first or second aspects of the invention, the expression cassette according to the third aspect of the invention or the recombinant plasmid according to the fourth aspect of the invention for specifically expressing a heterologous nucleic acid molecule in anther and/or pollen of a plant.

The heterologous nucleic acid may be one that has the function of inhibiting the formation of anthers and/or pollen. Use of such nucleic acid in the seventh, eighth, or ninth aspects of the invention allows the creation of male sterile plants. Alternatively, the heterologous nucleic acid may impart resistance to environmental stresses such as extremes of temperature, salinity, pests, infection or provide other desirable properties.

The invention also relates to propagation material of the transgenic plants of the sixth aspect of the invention, e.g. fruits, seeds, tubers, root-stocks, seedlings, cuttings etc.

BRIEF DESCRIPTION OF THE FIGURES

FIG. 4 shows the At39 gene nucleotide and protein sequence.
A. The At39 gene sequence contains 366 nucleotides (SEQ ID NO: 16), and encodes a protein containing 89 amino acids (SEQ ID NO: 2). The intron is shown in lowercase letters and comprises 96 base pairs. The deduced amino acid sequence is represented in single letter code. The At39 gene-specific primers are shown with arrows.
B. The hydropathicity plot of the At39 protein.

FIG. 5 shows the At39 promoter nucleotide sequence (SEQ ID NO. 1), showing the region-1850 bp upstream of the translational start site (shown in italics). The putative regulatory or tissue-specific motifs are indicated in bold. The location of promoter-specific primers is indicated by underlining. The restriction sites, Eco R1, Bcl 1, Ssp 1, Sph1, Hind 111 and BamH1 are shown in lower case.

FIG. 9 shows sequence alignment of the At39 promoter insert from the pDrive plasmid (top) (SEQ ID NO: 22) and the original promoter sequence (bottom) (SEQ ID NO: 23).

Lane 1. λ/Hind 111 ladder.
Lane 2. The At39 promoter fragment amplified during PCR using At39prom-5' and At39prom-3' primers from genomic DNA.
Lane 3. The empty pBI 101.3 vector digested with Bam H1 and Hind 111.
Lane 4. The pBI/At39 promoter plasmid digested with Bam H1 and Hind 111.
Lane 5. Eco R1 digestion of the pBI/At39 promoter plasmid.

FIG. 11 shows sequence of the At39 promoter (SEQ ID NO: 25) and GUS gene junction in the pBI plasmid to ensure the reporter gene will function correctly. The pBI/At39 plasmid (top) (SEQ ID NO:24) contains a linker region from the vector. The GUS translation start site is shown at +1080.

FIG. 12 shows PCR analysis to verify *Agrobacterium tumefaciens* contains the pBI/At39 promoter plasmid.
Lane 1. The λ/Hind 111 ladder.
Lane 2. PCR with At39prom-5' and At39prom-3' primers.
Lane 3. PCR with pBI-GUS forward and reverse primers.

Figure 13:
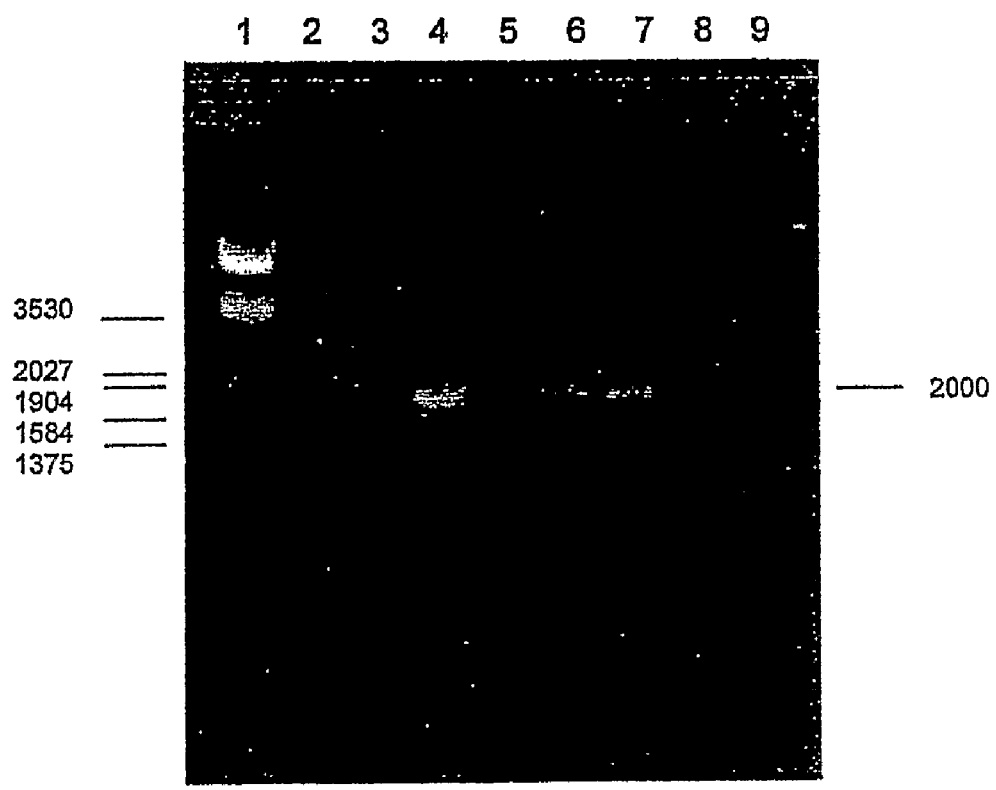

FIG. 13 shows confirmation the plants were transformed with the pBI/At39 promoter construct. Using PCR analysis of plant material with the pBI-GUS forward and reverse primers.
Lane 1. The λ-EcoR1/Hind 111 ladder.
Lane 2. Control using non-transformed tissue from a wild-type plant.
Lane 3-7. Transgenic plant lines 1-5 containing the promoter construct.
Lane 8. A plant line without the promoter construct.
Lane 9. Control using pBI/At39 plasmid DNA.

FIG. 14 shows At39 promoter-GUS expression in florets.
A. Flowers from plant line #3. GUS expression (blue) is evident in anthers.
B. Flowers from plant line #5. GUS expression is evident in the anthers and sepals.

Figure 15:
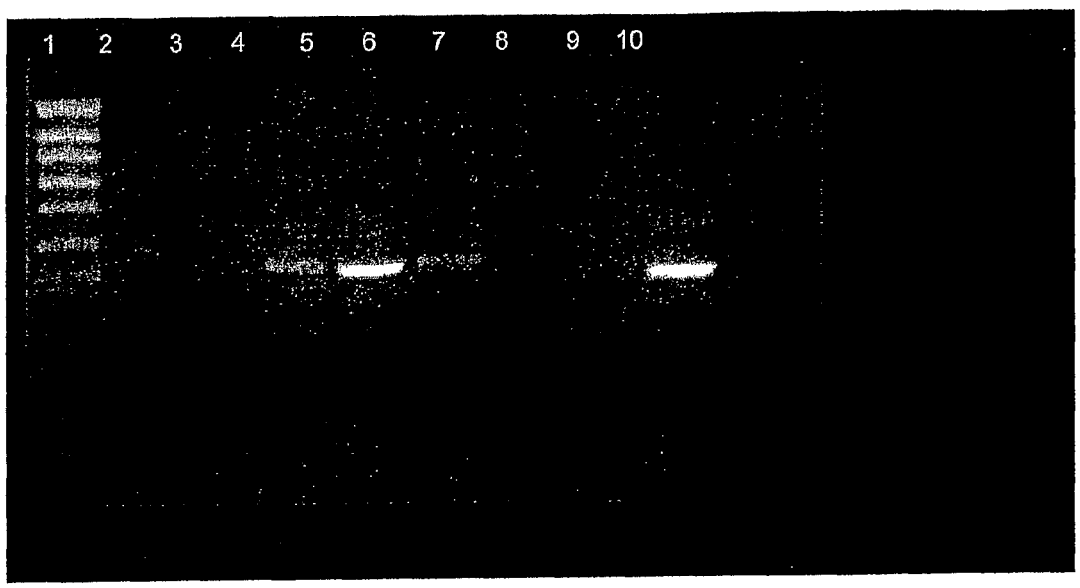

FIG. 15 shows *Triticum aestivum* Ta39 promoter expression. A 350 bp DNA band was amplified in lanes 4, 5 & 6. The PCR in these lanes was performed on cDNA samples prepared from three different flower tissues, and suggests that Ta39 is expressed in anther, gynocium and lemma and short awn cDNA.
Lane 1: Hyperladder IV
Lane 2: Template was wheat leaf cDNA (2 week old plants).
Lane 3: Template was wheat leaf cDNA (6 week old plants).
Lane 4: Template was wheat anther cDNA.
Lane 5: Template was wheat gynocium cDNA.
Lane 6: Template was wheat lemma & short awn cDNA.
Lane 7: Template was wheat stem cDNA.
Lane 8: Template was wheat young root cDNA (4 days after germination).
Lane 9: Positive control.
Lane 10: Negative control, no template added to this PCR

DETAILED DESCRIPTION OF THE INVENTION

The inventors have isolated promoters from *Arabidopsis thaliana*, *Triticum aestivum*, and canola which are primarily expressed in anther tissue. These promoters are particularly important in relation to legumes, crop, cereal and native grasses, fruiting plants, and flowering plants as they may provide means for increasing yield.

Arabidopsis has become the model system used for genetic analysis in plant molecular biology. It is ideal because of its small size, short life cycle and small genome. Self-fertilization results in large amounts of seed being produced, and efficient transformations systems are available. Importantly, Arabidopsis and Canola belong to the crucifer family and share significant genetic homology. As an appropriate promoter has been identified in Arabidopsis an ortholog is likely to exist in Canola. If a Canola promoter cannot be identified, the Arabidopsis anther-specific promoter could be used instead.

The nucleotide sequence of the Arabidopsis At39 gene was obtained from the Genbank database following a BLAST search, which was performed to identify a protein homologous to the tobacco TA39 protein (Goldberg, supra). The At39 gene encodes a protein that shares 30% homology with the TA39 protein. The nucleotide sequence of the At39 promoter is provided as SEQ ID NO: 1, the nucleotide sequence of the At39 gene is provided in FIG. 4 (SEQ ID NO: 16) and the amino acid sequence of the At39 polypeptide is provided in FIG. 4 (SEQ ID NO: 2). The TA39 polypeptide sequence is provided as SEQ ID NO: 3.

The nucleotide sequence of the *Triticum aestivum* Ta39 genes were obtained from the Genbank database following a search to identify proteins with sequence homology to the *Arabidopsis thaliana* At39 gene. The Ta39 genes encode proteins with 64% and 50% sequence identity to the tobacco At39 polypeptide and more than 90% sequence identity to the TA39 protein. The sequence of a Ta39 nucleic acid molecule is provided as SEQ ID NO: 12 and the corresponding Ta39 amino acid sequence is provided as SEQ ID NO: 13.

Tissue-specific promoters are important tools for research and may have useful applications in agricultural practices. Such applications include the development of a male sterility system that can be used to breed hybrid crops. The At39 promoter may be used to regulate gene expression in the anther region of crops such as Canola. Promoters are commonly interchangeable between a variety plant species. As with the tobacco TA39 promoter, the At39 promoter is active and is anther-specific in Brassica species.

As defined herein "isolated" means substantially free from material present in nature in the plant from which the nucleic acid molecule is derived, that is in an environment different from that in which the compound naturally occurs.

"Isolated" is meant to include compounds that are within samples that are substantially enriched for the compound of interest and/or in which the compound of interest is partially or substantially purified.

"Anther specific" is used herein to describe cDNAs, genomic DNAs and messenger RNAs which are associated with anther tissue. Such a promoter nucleic acid molecule directs expression almost exclusively to the male reproductive tissues, i.e. the anther and pollen, rather than to all plant cells. Such promoters may not solely direct expression to the anther or pollen, but will direct expression to the anther or pollen to a greater degree than to other cells or tissues. In the case of promoter DNA sequences, anther specific describes a regulatory sequence which directs the transcription of associated coding sequences so that when assayed through northern blot hybridisation, the mRNA corresponding to the heterologous sequence is present in anther and/or pollen cells or tissues in concentrations at least 10 times more than to other plant cells or tissues, preferably at least 20 times, more preferably at least 50 times and most preferably at least 100 times more to the anther and/or pollen cells or tissues than to other plant cells or tissues.

Anther tissue describes the tissue of the male reproductive organs in a plant, be it fully developed or partially developed. The definition of anther tissue used herein is intended to include all structures making up the anther, that is the epidermis, endothecium, middle layer and tapetum.

Because anther and pollen tissue are both involved in the male sexual function of a plant, a nucleic acid molecule may be considered to be "anther specific" for the purpose of the present invention if it is expressed specifically in pollen as well as in anther tissues.

Pollen is the haploid male gamete in flowering plants and carries the sperm cells required for fertilisation of the ovules. These tiny grains develop within the anther and are released as the anther matures by a process referred to as dehiscence.

As defined herein a "promoter" is the minimal nucleic acid molecule that specifically binds RNA polymerase to determine where transcription begins. Transcription is the production of RNA from the DNA template.

A promoter is the minimum sequence sufficient to drive transcription. "Promoter" is also meant to encompass those promoter elements sufficient for promoter-dependent gene expression controllable for cell-type specific, tissue-specific or inducible by external signals or agents; such elements may be located in the 5' or 3' regions of the native gene. As the promoters of the present invention are anther specific they can be used to direct expression to the anther of heterologous nucleic acid operably linked to the promoter.

"Promoter elements" as used herein refers to sub-domains within the promoter that confer tissue-specific expression, enhance expression, or inhibit expression. A promoter can contain a multiplicity of promoter elements. Furthermore, some elements can appear more than once within a single promoter. Examples of such elements are E-box motifs, RY-repeat elements, AT-rich regions, ACGT-core elements, Opaque-2-like elements, and conserved gymnosperm-like regions. Additional examples of promoter elements can be found in U.S. Pat. No. 5,723,751 to Chua; U.S. Pat. No. 5,608,149 to Barry et al.; U.S. Pat. No. 5,589,615 to De Clercq et al.; U.S. Pat. No. 5,589,583 to Klee et al.; U.S. Pat. No. 5,677,474 to Rogers; U.S. Pat. No. 5,487,991 to Vandekerckhove et al.; and U.S. Pat. No. 5,530,194 to Knauf et al. Typically, a TATA box is found on the 3'-end of the series of promoter elements.

Examples of specific promoter elements are provided below and in relation to the Figures. However, one of skill in the art will appreciate that a specific promoter element sequence provided can be modified while still maintaining activity. For example a base in an RY-repeat element can be changed without the RY-repeat element losing its functionality within the overall promoter sequence.

"Nucleic acid molecule" as used herein refers to an oligonucleotide, polynucleotide, nucleotide and fragments or portions thereof, as well as to peptide nucleic acids (PNA), fragments, portions or antisense molecules thereof, and to DNA or RNA of genomic or synthetic origin which can be single-or double-stranded, and represent the sense or antisense strand. Where "nucleic acid" is used to refer to a specific nucleic acid sequence "nucleic acid" is meant to encompass polynucleotides that encode a polypeptide that is functionally equivalent to the recited polypeptide, e.g., polynucleotides that are degenerate variants, or polynucleotides that encode biologically active variants or fragments of the polypeptide, including polynucleotides having substantial sequence similarity or sequence identity relative to the sequences provided herein.

The terms "nucleotide sequence" and "nucleic acid sequence" are used herein interchangeably.

"Polypeptide" as used herein refers to an oligopeptide, peptide, or protein. Where "polypeptide" is recited herein to refer to an amino acid sequence of a naturally-occurring protein molecule, "polypeptide" and like terms are not meant to limit the amino acid sequence to the complete, native amino acid sequence associated with the recited protein molecule, but instead is meant to also encompass biologically active variants or fragments, including polypeptides having substantial sequence similarity or sequence identify relative to the amino acid sequences provided herein.

A "homologue" is defined as a nucleic acid molecule sharing the same function as another nucleic acid molecule. Homologues are generally determined by sequence identity or similarity as defined by alignment using algorithms such as that in the Advanced BLAST2 service provides by EMBL.

"Orthologues" are nucleic acid or amino acid sequences that share a common ancestral sequence, but that diverged when a species carrying that ancestral sequence split into two species. Orthologous sequences are usually also homologous sequences.

In a preferred embodiment the homologues or orthologues encode or are cysteine rich peptides. In such peptides the cysteine-rich regions (roughly 12 cysteine residues over a 60 residue peptide) are highly homologous with more than 50% identity. However, the promoter nucleotide sequences of the genes encoding such peptides can vary greatly.

Homologous sequences are generally those with a percentage sequence identity of at least 50% at nucleotide or amino acid level according to BLAST analysis. Sequences that have identity of at least 50%, 60%, 70%, 80% and at least 90% that are functionally active are said to be homologous sequences.

"Percent (%) sequence identity" with respect to the nucleic acid sequences identified herein is defined as the percentage of nucleotides in a candidate sequence that are identical with the nucleotides in the specific nucleotide sequence, after aligning the sequences and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % nucleotide sequence identity values are generated using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. For purposes herein, a % nucleotide sequence identity value is determined by dividing (a) the number of matching identical nucleic acid residues between the nucleotide sequence of the promoter of interest having a sequence derived from the promoter and the comparison nucleotide sequence of interest (i.e., the sequence against which the promoter sequence of interest is being compared which may be a promoter variant) as determined by WU-BLAST-2 by (b) the total number of nucleotides of the promoter of interest.

Percent nucleic acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded. NCBI-BLAST2 uses several search parameters, wherein all of those search parameters are set to default values including, for example, unmask =yes, strand =all, expected occurrences =10, minimum low complexity length =15/5, multi-pass e-value =0.01, constant for multi-pass =25, dropoff for final gapped alignment =25 and scoring matrix =BLOSUM62.

"A homologue" as defined herein means a nucleic acid molecule which encodes an active promoter as defined below. In addition, a "homologue" has at least about 50% nucleic acid sequence identity with the nucleotide sequence shown as SEQ ID NO: 1 or the nucleotide sequence encoding the polypeptide having SEQ ID NO: 2 as disclosed herein, or any fragment thereof. Ordinarily, a homologue will have at least about 50% nucleic acid sequence identity, more preferably at least about 51% nucleic acid sequence identity, more preferably at least about 52% nucleic acid sequence identity, more preferably at least about 53% nucleic acid sequence identity, more preferably at least about 54% nucleic acid sequence identity, more preferably at least about 55% nucleic acid sequence identity, more preferably at least about 56% nucleic acid sequence identity, more preferably at least about 57% nucleic acid sequence identity, more preferably at least about 58% nucleic acid sequence identity, more preferably at least about 59% nucleic acid sequence identity, more preferably at least about 60% nucleic acid sequence identity, more preferably at least about 61% nucleic acid sequence identity, more preferably at least about 62% nucleic acid sequence identity, more preferably at least about 63% nucleic acid sequence identity, more preferably at least about 64% nucleic acid sequence identity, more preferably at least about 65% nucleic acid sequence identity, more preferably at least about 66% nucleic acid sequence identity, more preferably at least about 67% nucleic acid sequence identity, more preferably at least about 68% nucleic acid sequence identity, more preferably at least about 69% nucleic acid sequence identity, more preferably at least about 70% nucleic acid sequence identity, more preferably at least about 71% nucleic acid sequence identity, more preferably at least about 72% nucleic acid sequence identity, more preferably at least about 73% nucleic acid sequence identity, more preferably at least about 74% nucleic acid sequence identity, more preferably at least about 75% nucleic acid sequence identity, more preferably at least about 76% nucleic acid sequence identity, more preferably at least about 77% nucleic acid sequence identity, more preferably at least about 78% nucleic acid sequence identity, more preferably at least about 79% nucleic acid sequence identity, more preferably at least about 80% nucleic acid sequence identity, more preferably at least about 81% nucleic acid sequence identity, more preferably at least about 82% nucleic acid sequence identity, more preferably at least about 83% nucleic acid sequence identity, more preferably at least about 84% nucleic acid sequence identity, more preferably at least about 85% nucleic acid sequence identity, more preferably at least about 86% nucleic acid sequence identity, more preferably at least about 87% nucleic acid sequence identity, more preferably at least about 88% nucleic acid sequence identity, more preferably at least about 89% nucleic acid sequence identity, more preferably at least about 90% nucleic acid sequence identity, more preferably at least about 91% nucleic acid sequence identity, more preferably at least about 92% nucleic acid sequence identity, more preferably at least about 93% nucleic acid sequence identity, more preferably at least about 94% nucleic acid sequence identity, more preferably at least about 95% nucleic acid sequence identity, more preferably at least about 96% nucleic acid sequence identity, more preferably at least about 97% nucleic acid sequence identity, more preferably at least about 98% nucleic acid sequence identity and yet more preferably at least about 99% nucleic acid sequence identity with the nucleic acid sequence of SEQ ID NO:1 or the nucleic acid sequence encoding the polypeptide sequence shown as SEQ ID NO: 2.

Persons skilled in the art would readily be able to determine if a homologue, orthologue, fragment or variant of the sequence provided according to SEQ ID NO: 1 functions as an anther specific promoter and accordingly falls within the scope of the claims. An example of a test to see if a sequence acts as an anther specific promoter in accordance with the present invention the sequence under test is fused in frame with the GUS reporter gene in a binary vector. Agrobacterium containing the putative promoter/GUS binary vector is used to transform plant tissues from which plantlets are regenerated. Tissues from the transgenic plants at various stages of development are assayed for GUS expression using X-GLUC as substrate, whereby GUS expression in anther tissue shows that the sequence under test is an anther specific promoter and falls within the scope of the invention.

Complementary as used herein in relation to nucleic acid molecule "complementary" to the nucleic acid sequence of (a), (b) or (c) is intended to encompass those sequences that are capable of hybridising under high stringency conditions to the nucleic acid molecules defined.

"Hybridisation" in relation to nucleic acids is the forming of a hybrid of two single complementary strands of nucleic acid to form a double strand.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1994) and Sambrook et al., Molecular Cloning, A Laboratory Manual, 2nd Edition (1989) Cold Spring Harbor Laboratory Press, Cold Spring Harbor, N.Y.).

Reference herein to "high stringency conditions" may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50µ/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1× SSC containing EDTA at 55° C.

A "fragment" is defined as a portion or domain of the full length sequence provided according to the present invention, which fragment maintains the capacity to direct expression of heterologous nucleic acid to which it is operably linked to anther or pollen tissue in plants.

Experiments to ascertain if a fragment maintains the ability of the full length sequence to direct expression of heterologous nucleic acid to which it is operably linked to anther or pollen tissue in plants are provided in the Examples section.

Ordinarily, the anther specific promoter fragment is at least about 30 nucleotides in length, often at least about 60 nucleotides in length, more often at least about 90 nucleotides in length, more often at least about 120 nucleotides in length, more often at least about 150 nucleotides in length, more often at least about 180 nucleotides in length, more often at least about 210 nucleotides in length, more often at least about 240 nucleotides in length, more often at least about 270 nucleotides in length, more often at least about 300 nucleotides in length, more often at least about 450 nucleotides in length, more often at least about 600 nucleotides in length, more often at least about 900 nucleotides in length, more often at least about 1000 nucleotides in length, more often at least about 1200 nucleotides in length, more often at least about 1400 nucleotides in length, more often at least about 1600 nucleotides in length, more often at least about 1800 nucleotides in length, more often at least about 1850 nucleotides in length, or more.

"Derivatives" of nucleic acid molecules or proteins or peptides as defined herein encompass those molecules comprising non-naturally occurring residues or those naturally occurring residues that have been modified by chemical or other means.

"Derivatives" as used herein in relation to nucleic acid molecules, proteins and peptides are also intended to encompass single or multiple nucleotide or amino acid substitutions, deletions and/or additions as well as parts, fragments, portions, homologues and analogues of the nucleic acid molecule or protein or peptide.

A "transformed" cell is a cell into which a nucleic acid molecule has been introduced by molecular biology techniques. As used herein, the term "transformation" encompasses all techniques by which a nucleic acid molecule might be introduced into such a cell, including transfection with a viral vector, transformation with a plasmid vector, and introduction of naked DNA by electroporation, lipofection, and particle gun acceleration.

In this context "heterologous" nucleic acid means that the nucleic acid introduced into transformed cells is a nucleic acid not naturally occurring in the cells in this form. On the one hand, it may be nucleic acid which does naturally not at all occur in these transformed cells or nucleic acid which, even if it does occur in these cells, is integrated at other genetic positions as exogenous nucleic acid and is therefore situated within another genetic environment.

The heterologous nucleic acid whose expression is to be directed specifically to anther tissue may be any nucleotide sequence that is desirable to be introduced. For example, it may be desirable to provide a transgenic plant in which the anthers express a gene which confers resistance to pathogens, insects and pests, or a gene which confers resistance to stresses such as extremes of temperature, for example a frost resistance gene. Frost resistance genes include dehydrin genes, genes coding for CBF transcription factors and genes in the CBF regulon (CBF-targeted genes). Genes coding for protease inhibitors and $B_t$ toxins may be included to provide resistance to pathogens, insects and pests.

In a particularly preferred embodiment the heterologous nucleic acid is antisense to a gene(s) involved in pollen development, such that transformation of a cell with the vector according to one aspect of the invention turns off expression of the gene(s) involved in pollen development, thereby producing male sterile plants.

Preferably the male sterile plants may be produced by RNA interference utilising antisense nucleic acid molecules against one or more genes involved in pollen development, such as BnMYB103 as described in our co-pending application.

"Antisense nucleic acid molecules" as described herein defines sequences that are complementary to a gene of interest or part thereof. Such antisense nucleic acid molecules, may bind to the endogenous gene and block prevent expression of the functional gene in a plant cell. Antisense techniques generally use short 10 to 20 oligonucleotide fragments which hybridise to essential parts of the gene thereby blocking its expression. Such essential regions of the gene may include regions within the 5' regulatory region such as enhancer and promoter regions and may also include the transcription start site.

In another embodiment, the present invention contemplates a method of inducing or otherwise facilitating male sterility in a plant, said method comprising operably linking a cytotoxic nucleic acid molecule to the anther specific promoter according to one aspect of the invention, such that upon expression of the promoter, the cytotoxic nucleic acid molecule is expressed to produce a product that inactivates, kills or otherwise renders substantially non-functional male gametes in said transformed plant.

The plant may be a monocotyledonous or dicotyledonous plant. The invention is particularly important in relation to legumes, crop, cereal and native grasses, fruiting plants, and flowering plants as it provides means for increasing yield. Preferred plants according to the present invention include, but are not limited to, the Brassicaceae and other Solanaceae species such as potato and the cole vegetables cabbage, kale, collards, turnips, rutabaga, kohlrabi, Brussels sprouts, broccoli and cauliflower, the mustards and oilseeds, crucifers, broccoli, canola, tomato, grain legumes, wheat, barley, maize, tobacco, rice, and the like. A particularly preferred model system for research is Arabidopsis. Particularly preferred plants are canola and wheat.

An "expression cassette" according to the present invention is a nucleic acid molecule made up of at least the anther specific promoter and a site for inserting heterologous nucleic acid such that the expression of the heterologous nucleic acid in a transformed cell is driven by the anther specific promoter.

The expression cassette will preferably comprise at least one restriction enzyme site to facilitate insertion of the heterologous nucleic acid.

The expression cassette preferably comprises the anther specific promoter operably linked to heterologous nucleic acid.

In practice, the expression cassette used to transfect the plant nucleus will generally additionally comprise various control elements. Such control elements may include a ribosome binding site (RBS), positioned at an appropriate distance upstream of a translation initiation codon to ensure efficient translation initiation.

Expression cassettes envisaged according to the present invention include those comprising an anther specific promoter and at least one heterologous nucleic acid fragment or gene.

A person skilled in the art will be readily able to determine suitable expression cassettes.

Preferably most or all of the constituents of the expression cassette are operably linked.

A "recombinant" nucleic acid is one having a sequence that is not naturally occurring or having a sequence made by an artificial combination of two otherwise separated sequences. This artificial combination is often accomplished by chemical synthesis or, more commonly, by the manipulation of isolated segments of nucleic acids, e.g., by genetic engineering techniques.

The anther specific promoter and heterologous nucleic acid may be used to transformed a cell by any means known in the art. Preferably the expression cassette is provided in a vector.

A "vector" is a nucleic acid molecule as introduced into a host cell, thereby producing a transformed host cell. A vector may include one or more nucleic acid sequences, such as an origin of replication, that permit the vector to replicate in a host cell. A vector also may include one or more selectable marker genes and other genetic elements known in the art.

The term "vector" as used herein is intended to encompass any carrier for nucleic acid, including plasmids and phage.

As used herein a "transgenic plant" refers to a plant that contains recombinant genetic material ("transgene") not normally found in a wild-type plant of the same species. Thus, a plant that is generated from a plant cell or cell line into which recombinant DNA has been introduced by transformation is a transgenic plant, as are all offspring of that plant containing the introduced transgene (whether produced sexually or asexually).

As used herein a "cell line" is a population of cells which has been maintained in a culture for an extended period.

The present invention provides transformed cells comprising a nucleic acid molecule or fragment thereof according to one aspect of the invention or an expression cassette or a plasmid according to other aspects of the invention. By means of methods known to the skilled person the transgenic plant can be generated from a transgenic plant cell. Thus, the plants obtained from the transgenic plant cells of the invention are also the subject-matter of the present invention. The present invention also extends to plants which contain the above-described transgenic plant cells. The transgenic plants may in principle be plants of any desired species as previously defined.

For the purposes of this specification it will be clearly understood that the word "comprising" means "including but not limited to", and that the word "comprises" has a corresponding meaning.

It will be clearly understood that, although a number of prior art publications are referred to herein, this reference does not constitute an admission that any of these documents forms part of the common general knowledge in the art, in Australia or in any other country.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Embodiments of the present invention will now be described in the following non-limited examples.

EXAMPLES

1. Identification of TA39 Gene Orthologue in *Arabidopsis thaliana*

Figures 1, 2:
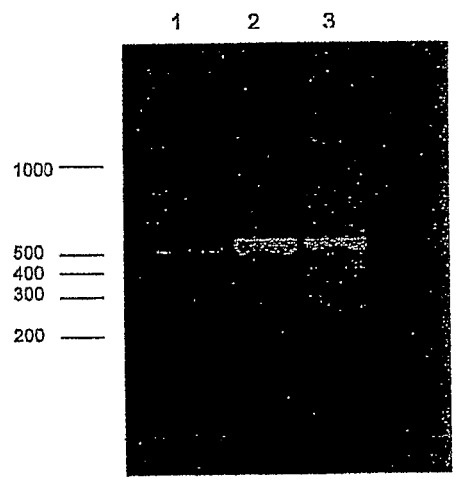
FIG. 1 provides a sequence alignment of TA39 (top) (SEQ ID NO:3) and At39 protein sequences from a BLAST search residues 6 to 74 of SEQ ID NO:2). The two proteins show 30% identity in amino acid sequence and a further 10% of the amino acids are similar (shown as +). Ten gaps were introduced to provide the best possible alignment.
FIG. 2 shows RT-PCR analysis of floral RNA using tubulin primers. Lane 1. 100 bp DNA ladder (Promega). Lane 2. The 500 bp tubulin product amplified from cDNA generated with the tubulin reverse primer. Lane 3. The 500 bp tubulin product amplified from cDNA generated with the poly(T) primer.

The tobacco TA39 protein amino acid sequence (SEQ ID NO: 3) was used to identify an orthologous protein in *Arabidopsis thaliana*. A BLAST search was performed using the National Centre for Biotechnology Information database. Several proteins were found showing similarities to the TA39 protein. The protein most similar in length, and with the greatest amount of sequence similarity was chosen for further investigation. The *Arabidopsis thaliana* gene designated At39 encodes a protein that shows 30% identity with the TA39 protein and a further 10% of the amino acids were not identical, but are similar in structure allowing for conservative substitutions (FIG. 1). Oligonucleotide primers specific for the coding and promoter regions of the At39 gene were designed.

2. Tissue-specificity of the At39 Gene

RT-PCR analysis was used to ascertain the abundance of the Arabidopsis At39 gene transcripts in various tissues and to determine if the At39 gene has a similar expression pattern to the TA39 gene.

The RNA used for the RT-PCR reactions was isolated from leaf, flower and root tissues harvested from wildtype *A. thaliana* plants (ecotype Columbia). RNA products were visualized on a 1% agarose gel stained with ethidium bromide.

Controls were required to ensure an equivalent amount of RNA was used from each tissue. Several RT-PCR reactions were performed using tubulin primers to quantify the amount of RNA used in each reaction. The tubulin reverse primer was used to generate the cDNA template from RNA samples. However, the RT-PCR only amplified a tubulin product from flower RNA and not from leaf or root RNA. Another primer, poly-T (PE Biosystems) was used to obtain the cDNA template. However, once again tubulin primers amplified a product from the flower RNA but not from the root or leaf RNA. In FIG. 2, lanes 2 and 3 show the 500 bp tubulin product amplified cDNA generated from floral RNA.

The RT-PCR was repeated several times with slight variations each time in an attempt to obtain tubulin products from leaf and roots, but to no avail.

3. Identification of At39 Gene Orthologue in *Triticum aestivum* and its Tissue Specificity The *Arabidopsis thaliana* At39 amino acid sequence as identified in Example 1 was used to identify orthologous proteins in *Triticum aestivum*. A BLAST search was performed using the Grain Gene database (http://wheat.pw.usda.gov). Several proteins were found showing sequence similarity to the At39 protein. The proteins most similar in length, and with the greatest amount of sequence similarity, were chosen for further investigation.

The *Triticum aestivum* genes, designated Ta39-1 (SEQ ID NO: 12) and Ta39-2 encode proteins that show 64% and 50% sequence identity respectively with the At39 protein and have about 80% sequence identity to the tobacco TA39 gene. The deduced amino acid sequences of the Ta39-1 (SEQ ID NO:13) and Ta39-2 genes show more than 90% sequence identity to the TA39 protein from tobacco.

Oligonucleotide primers (TGCAACTGCGTGC-CGTCGGGGAC, SEQ ID No: 14 and AACAAGGAC-GAGTGCCCCCTGCTAC, SEQ ID No: 15) specific for the coding and promoter regions of the Ta39-1 and Ta39-2 genes were designed.

RT-PCR analysis was used to ascertain the abundance of the Ta39-1 and Ta39-2 gene transcripts in various tissues and to determine if the Ta39-1 and Ta39-2 genes have a similar expression pattern to the At39 gene from Arabidopsis.

The RNA used for the RT-PCR reactions was isolated from anther, spiklet (flower), leaf, stem and root tissues harvested from *T. aestivum*. RNA products were visualized on a 1% agarose gel stained with ethidium bromide. The tubulin reverse primer was used to generate the cDNA template from RNA samples. As shown in FIG. 15, the RT-PCR amplified a tubulin product from spiklet and anther RNA. No product was amplified from leaf, stem or root RNA.

4. Cloning the At39 Gene and Promoter Region

Figure 3:
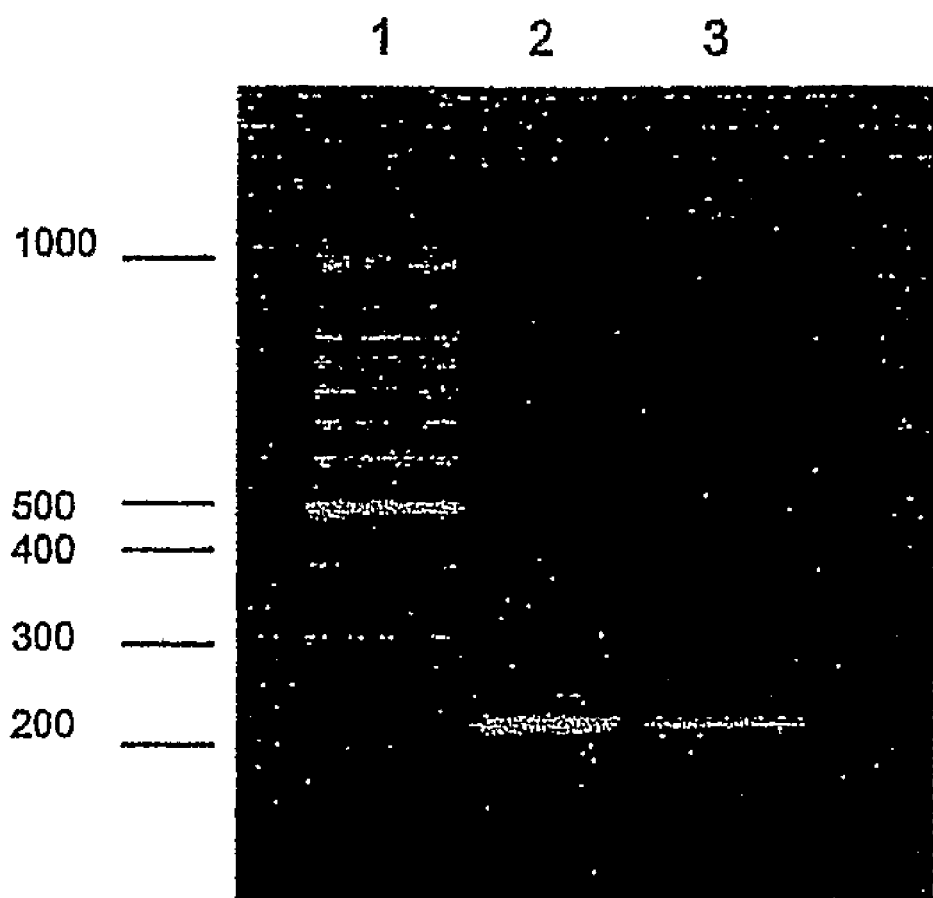
FIG. 3 shows the cDNA clone of the At39 gene. Using cDNA obtained from RNA as the template for the PCR with At39 gene-5' and 3' primers.
Lane 1. 100 bp DNA ladder.
Lane 2 and 3. The 200 bp At39 gene fragment

The cDNA produced from flower tissue during the RT-PCR reaction of Example 2 was used to amplify the Arabidopsis At39 gene. A cDNA clone of the At39 gene was obtained from a PCR using the At39 gene 5' and 3' primers. The PCR product was run on a 1% agarose gel (FIG. 3). The 200 bp cDNA clone of the At39 gene is shown in lanes 2 and 3.

The At39 gene fragment was isolated from the gel and the purified cDNA was sequenced to confirm that the desired gene had been cloned. The sequence was also used to determine the size and location of the intron. The At39 gene sequence is shown in FIG. 4. (SEQ ID NO: 16). The gene is 366 bp in length and contains a 96 bp intron. The deduced peptide sequence (SEQ ID NO: 2). reveals the gene codes for a protein 89 amino acids long. Several differences were observed between the cloned At39 gene sequence and the sequence obtained from the Genbank database. The cloned gene encodes a protein of 89 amino acids rather than 58. There were also discrepancies associated with the position of the intron. The exon begins at position +178 rather than +174. The promoter region of the At39 gene was cloned from at position +178 rather than +174. The promoter region of the At39 gene was cloned from genomic DNA extracted from *Arabidopsis thaliana* (ecotype Columbia). The PCR reaction was performed using At39 prom-5' and 3' primers. The PCR product was run on a 1% agarose gel to confirm the presence of the 1.9 kb promoter fragment. The nucleotide sequence of the At39 promoter obtained from the Genbank database is shown in FIG. 5 (SEQ ID NO: 1), the binding positions of the promoter-specific primers are represented. A number of short sequences are also highlighted these are putative regulatory element from other anther/pollen-specific promoters, which are considered important for tissue-specificity.

5. Construction of the At39 Promoter Expression Vector

Figure 6:
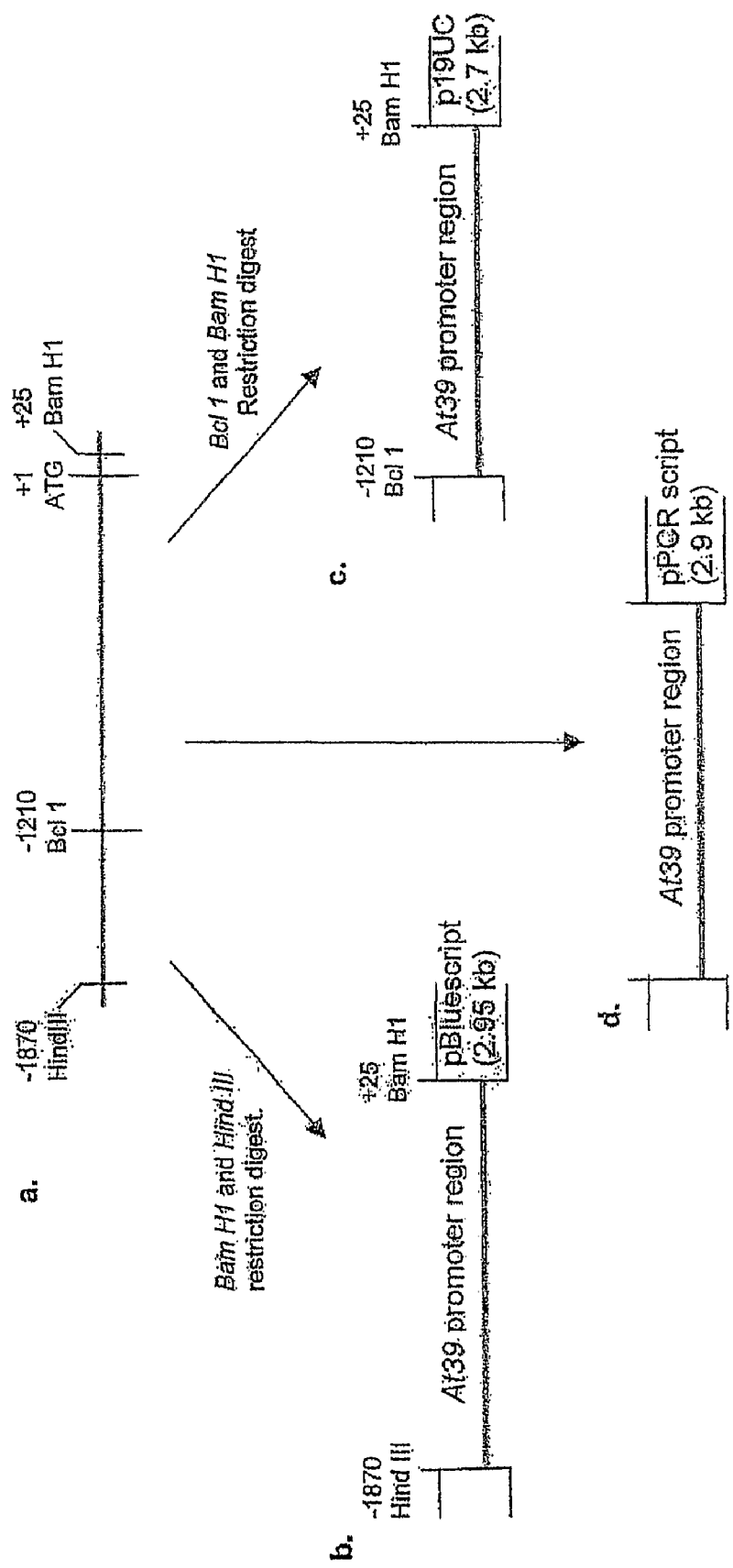
FIG. 6 shows the strategies attempting to clone the At39 promoter region into a high copy number vector.
a. The 1.9 kb At39 promoter fragment obtained from PCR using At39prom-5' and At39prom-3' primers.
b. The digested 1.9 kb At39 promoter cloned into the Bam H1 and Hind 111 restriction sites in pBluescript.
c. The 1.7 kb At39 promoter digest with Bcl 1 and Bam H1 cloned into p19UC.
d. The blunt ended 1.9 At39 promoter PCR product inserted into the PCR cloning site in pPCR script plasmid.

The At39 promoter fragment was digested with Bam H1 and Hind 111 restriction enzymes and ligated into pBluescript vector (Stratagene). The resulting plasmid was transformed into electro-competent *E. coli* (DH5α) cells, and selected using ampicillin resistance and blue/white screening. The success of the cloning was determined with restriction digestion to determine if the plasmid contained the insert. After numerous unsuccessful attempts, cloning the At39 promoter into pBluescript was never achieved. Other cloning strategies were considered. The promoter insert was digested with Bcl 1 and Bam H1 restriction enzymes to produce a smaller fragment 1200 bp in size, and ligated into the p19UC vector (2.5 kb). Stratagene's pPCR script was also utilised, which is a pre-digested, blunt ended vector designed for the direct cloning of PCR products. The only requirement is that the PCR products must be blunt-ended to remove A-overhangs. Using this vector avoids any problems encountered due to incomplete restriction digests of the insert or vector DNA. After many attempts, none of these cloning techniques were successful. The strategies attempting to clone the At39 promoter into pBluescript, p19UC and pPCR script are outlined in FIG. 6.

Figure 7:
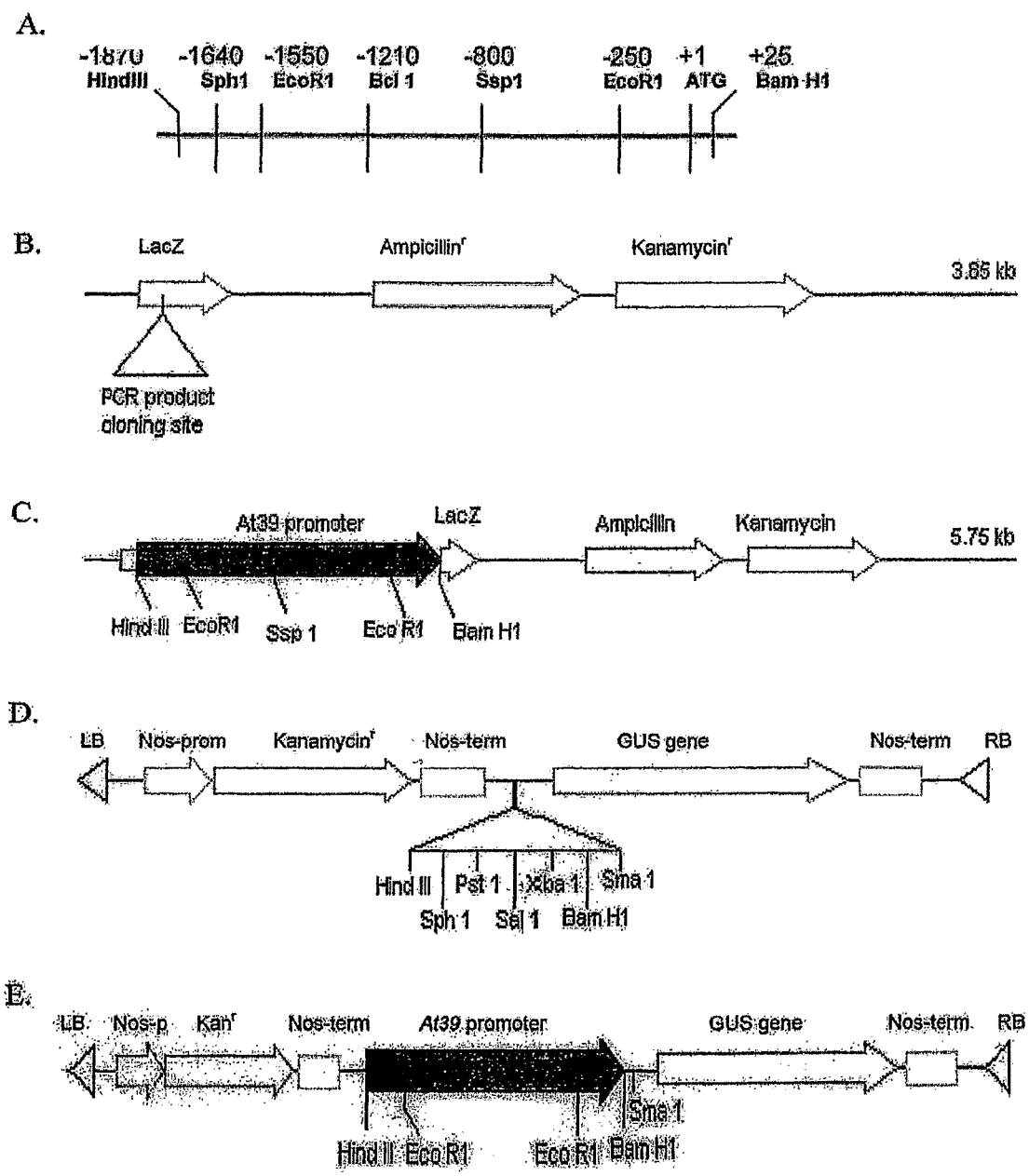
FIG. 7 shows the cloning strategy to produce the At39 promoter expression vector.
A. The 1.9 kb At39 promoter region showing the restriction sites and translational start site (ATG).
B. The 3.85 kb pDrive plasmid showing the PCR product cloning site.
C. The 1.9 kb At39 promoter inserted into the pDrive PCR product cloning site to create the 5.75 kb pDrive/At39 promoter plasmid.
D. The promoterless pBI101.3 binary vector.
E. The 1.9 kb At39 promoter digested from pDrive with Bam H1 and Hind 111 and cloned into pBI101.3 to produce the 14.1 kb pBI/At39 plasmid.

The QIAGEN pDrive cloning kit, consisting of the pDrive cloning vector (3.85 kb) designed for the direct cloning of PCR products, was used in a new cloning strategy (FIG. 7). The At39 promoter PCR product was ligated into pDrive. The resulting plasmid was transformed into electro-competent *Esherichia coli* (DH5α) cells and selected using ampicillin resistance and blue/white screening. Restriction digests with BamH1 and Hind111 confirmed the cloning success by releasing the fragment from the vector.

Figure 8:
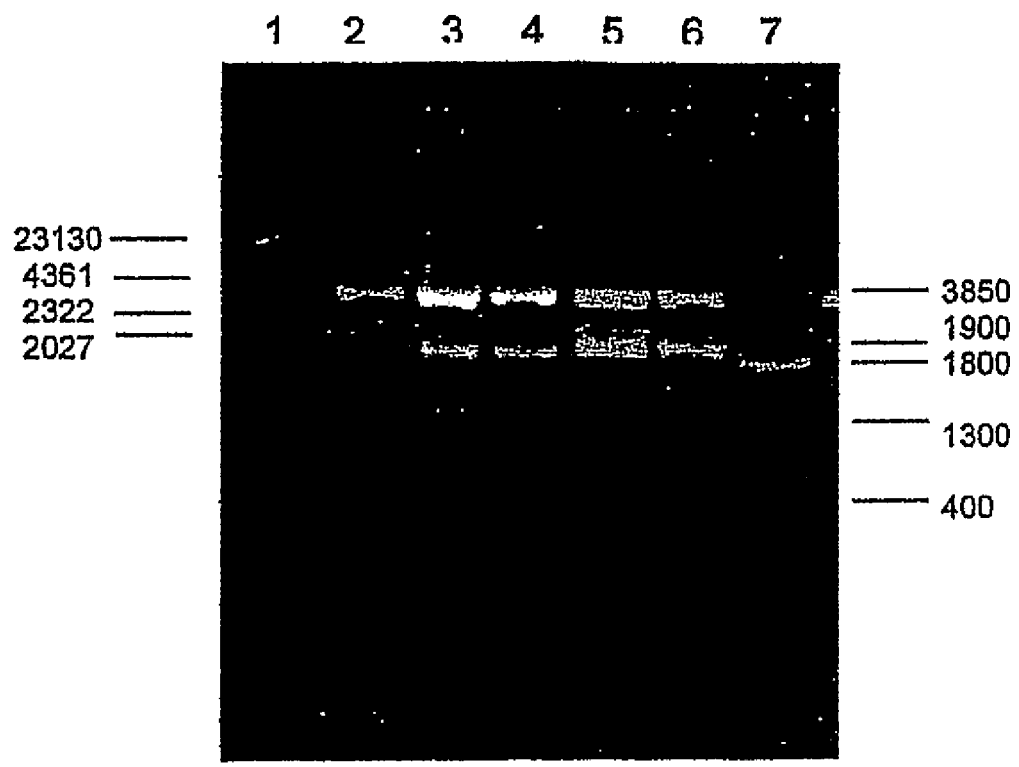
FIG. 8 shows identification of At39 promoter inserts cloned into the pDrive plasmid.
Lane 1. λ/Hind 111 ladder.
Lane 2. The pDrive plasmid without an insert.
Lane 3 and 5. The pDrive plasmid clones (B1 and B2) digested with Hind 111.
Lane 4 and 6. The pDrive plasmid clones digested with Bam H1.
Lane 7. The pDrive plasmid (B2) digested with Eco R1.

The first positive clone was verified with a triple restriction digest using Bam H1, Hind 111 and Sph1 but the expected fragments sized 3.85 kb, 1.7 kb and 0.2 kb were not obtained. Another triple digest using Ssp1 instead of Sph1 produced the expected band sizes 3.85 kb, 1.1 kb and 0.8 kb visible on a 1% agarose gel. This confirmed the At39 promoter had been cloned, but the failure of Sph 1 to digest the insert suggests the sequence may contain errors. The pDrive/At39 plasmid was sequenced using the universal M13 reverse primer. The sequence revealed the At39 promoter insert contained a base substitution at the Sph 1 restriction site and other significant errors. As the first At39 promoter clone was incomplete other pDrive white colonies were screened using restriction digestion with a single enzyme, either Bam H1 or Hind 111. The single enzyme digestion releases the insert from the plasmid due to presence of the restriction site on the end of the insert and one in the plasmid. Indicating each end of the At39 promoter fragment is intact. FIG. 8 shows the successful digestion of two pDrive clones B1 and B2. Lane 2 represents the pDrive vector without the insert. Lanes 3 and 5 show the pDrive vector digested with Hind 111, while 4 and 6 show the pDrive vector digested with Bam H1. The restriction digest of the pDrive/At39 (B2) plasmid with Eco R1 is shown in lane 7. The At39 promoter insert contains the correct number of restriction sites producing the expected sized fragments, namely 1.8 kb, 1.3 kb and 0.4 kb. This verified the insert is correct and was subsequently used for cloning.

The pDrive/At39 plasmid was sequenced using the M13 reverse primer to ensure the clone did not contain errors in the sequence. FIG. 9 shows the sequence alignment of the pDrive/At39 clone (SEQ ID NO: 22) and the original At39 promoter sequence (SEQ ID NO: 23). The At39 promoter clone matches closely with the original sequence, proving the errors found in the first clone were not generated during the PCR reaction. The At39 promoter insert was isolated from the pDrive/At39 vector following a double digestion using Bam H1 and Hind111, and cloned into the pBI101.3 binary vector. The resulting plasmid was transformed into electro-competent *E. coli* (DH5α) cells, and transformants were selected using kanamycin resistance. A control transformation was also performed, involving the self-ligated pBI101.3 vector without any insert DNA transformed into *E. coli* electro-competent cells. Due to the different cohesive ends the vector should not self-ligate and colonies cannot grow. If the control transformation produces a large number of colonies it indicates the restriction digestion of the vector was incomplete and it is unlikely that the At39 promoter insert has been incorporated into the binary vector.

Figure 10:
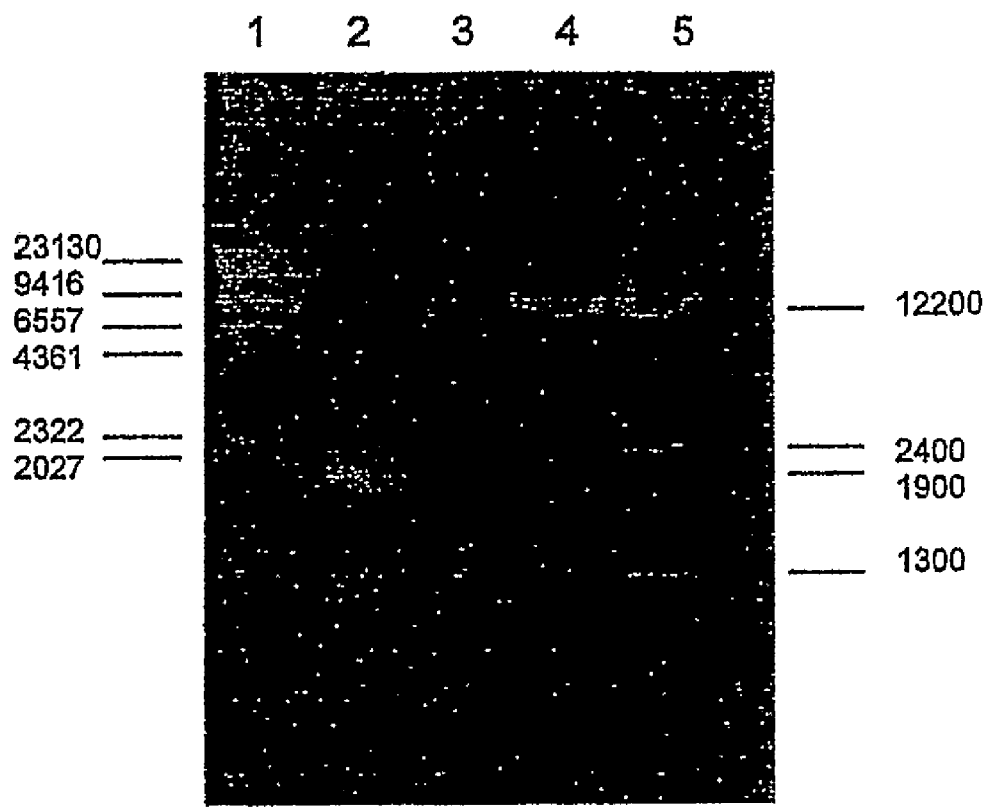
FIG. 10 shows cloning the At39 promoter into the pBI expression vector.

The successful cloning of the At39 promoter inserts into the pBI vector were confirmed with restriction digestion using Bam H1, Hind 111 and Eco R1 (FIG. 10). The At39 promoter PCR product (lane 2) acts as a control to compare the size of the cloned At39 promoter. The pBI101.3 vector digested with Bam H1 and Hind 111 is shown without an insert in lane 3, while lane 4 shows the 1.9 kb At39 promoter insert released from the vector. Lane 5 represents the pBI/At39 plasmid digested with Eco R1. The expected band sizes were present, namely 12.2 kb, 2.4 kb and 1.3 kb fragments.

To ensure the At39 promoter was cloned into the vector in the correct reading frame to regulate GUS expression, the junction between the At39 promoter and GUS gene was sequenced. FIG. 11 shows a portion of the sequence alignment comparing the plasmid (SEQ ID NO: 24), and original At39 promoter (SEQ ID NO:25) sequences. The sequences are identical, except for the complementary region due to the binding position of the reverse primer. The pBI/At39 promoter sequence (shown on the top) contains extra bases from the linker region on the pBI101.3 vector. The GUS gene translation start site (ATG) starts at position 1078 bp.

6. Transformation of *Arabidopsis thaliana*

The pBI/At39 promoter binary vector was transformed into *Agrobacterium tumefaciens* strain GV3101 by electroporation, using rifampicin, gentamycin and kanamycin selection. The presence of the transformed plasmid was confirmed by PCR analysis. The PCR products were run on a 1% agarose gel (FIG. 12). The PCR product obtained with the At39 promoter-specific primers is shown in lane 2, and the PCR product amplified with the PBI-GUS primers is shown in lane 3. The PBI-GUS primers bind each side of the multiple cloning sites in the pBI vector. *Agrobacterium* containing the pBI/At39 promoter plasmid was used to transform *Arabidopsis thaliana* (ecotype Landsberg erecta) using vacuum infiltration. The transformed plants yielded a large number of seeds, which were subsequently harvested and germinated with kanamycin selection and timentin to kill the *Agrobacterium*. The seedlings with kanamycin resistance were subjected to PCR analysis to confirm transformation had occurred (FIG. 13). As the At39 promoter-specific primers would amplify the endogenous At39 promoter, they were not suitable to confirm the promoter construct had been incorporated into the plant genome. Hence, the PCR was performed using the PBI-GUS primers. Lane 2 represents the PCR using leaf tissue from a wildtype non-transformed plant. Lanes 3-7 show the 2 kb fragment amplified from leaf tissue harvested from five transformed plant lines. Lane 9 is a control, the fragment was produced using pBI/At39 plasmid DNA. The bands are all identical in size demonstrating plant lines 1-5 had been transformed with the promoter construct. Plant line 6 (lane 8) did not amplify the fragment, indicating this plant is not transgenic.

7. Analysis of GUS Expression Pattern

The five transgenic lines were analysed for GUS expression. Due to the small size of the plants only a limited amount of tissue could be collected. A leaf and a single floret were removed from each line. Line 3 contained a number of flowers so the whole bolt was removed to encourage secondary flowering. Line 5 was infected with fungal contamination and was dying, so the whole plant was used for GUS staining.

The plants were incubated in the GUS substrate for 6 hours, but strong GUS expression was observed in the anther region after two hours (FIG. 14). GUS expression was located in the anther tissue for each plant line, however lines 2 and 5 also contained GUS expression in the sepals. GUS expression was not observed in any other tissue.

Discussion

The project has identified a novel promoter from *Arabidopsis* that is primarily expressed in anther tissue. A number of putative regulatory elements that direct tissue specificity were also identified.

1. The At39 Promoter

The nucleotide sequence of the Arabidopsis At39 gene was obtained from the Genbank database following a BLAST search, which was performed to identify a protein homologous to the tobacco TA39 protein. The At39 gene encodes a protein that shares 30% homology with the TA39 protein.

The promoter region of the At39 gene was amplified using PCR and cloned into an expression vector containing the GUS reporter gene. Promoter-GUS fusions resulted in GUS expression in anthers, demonstrating that At39 is strongly expressed in the anther region of Arabidopsis plants. Anther-specific promoters commonly contain short regulatory sequences that are sufficient to direct tissue-specific expression, and upstream regions that are important for higher levels of activity. Key features are conserved among tissue-specific promoters. These include consensus sequences common to some anther-specific promoters, however an element regulating anther-specific expression is yet to be identified that is common to all anther-specific promoters.

The At39 promoter contains a number of sequences in common with other anther-specific promoters. The AAATGA motif, originally identified in tobacco, occurs twice in the At39 promoter at position −1339 and −440. This motif is also shared with P0149 an anther-specific promoter from alfalfa. The CCACAAAAA sequence at position −240 is also shared with the chiA gene from petunia, and is highly conserved in other chalcone flavanone isomerase (chi) promoters. The TGAACG sequence located at −900 is present in the nopaline synthase (nos), the cauliflower mosaic virus 35S, and the pollen-specific Brassica napus Bp 19 promoters. The TATATATA site at position −1230 is also present in the A9 gene from Arabidopsis. However, the At39 promoter does not contain elements identical to the 52/56 or 56/59 boxes from the tomato LAT gene promoters.

The At39 and TA39 protein sequences share limited homology, and the promoter regions are even less similar. Nevertheless, the two genes exhibit similar expression patterns in anthers. There are some short sequences that are shared between the two promoter regions. The shared sequence TTGATATCCTT occurs at position −1450 in the At39 promoter. This region is a considerable distance upstream of the translational start site and is unlikely to be involved in tissue-specific gene expression. Other short sequences containing single base changes occur throughout the promoter regions. The TAA(C/G)TTTG sequence occurs at position −1128, TA(C/T)AAT at position −1096, GTCCT (C/G)AA at position −915, TT(G/C)TGA at position −747, T(A/T)TTGT at position −739, and ATGCAGATTT at position −500. These sequences occur a considerable distant upstream of the coding region and might not play a regulatory role. Both promoters contain high proportions of A and T residues, which may account for the short sequence similarities.

The TA39 promoter is primarily expressed in the tapetum layer of anthers. The actual site of At39 expression is not determined, as cross-sections of the anther have not yet been prepared. The At39 gene may be expressed throughout the anther or in a specific region such as the tapetum, middle layer or locule. GUS expression was detected in other tissue in only two transgenic lines. In these plants GUS expression occurred in the sepals as well as anthers. Only a limited number of plant lines were analysed for GUS expression patterns because the plants were required to be at the flowering stage of development. GUS expression in the sepal may be related to the developmental stage of the flower at the time of staining, or be caused by other factors such as a positional effect with respect to integration of the transgene. Whether At39 expression occurs in sepals can be best ascertained using in situ hybridisation.

The At39 gene encodes an 89 amino acid protein with a molecular weight of 9.75 kDa, while the TA39 protein encodes a 110 amino acid protein with a molecular weight of 11.9 kDa. The functions of the two proteins are not known, although they may be involved in pollen development. The mRNA from anther-specific genes may be pre-synthesised and stored in the pollen grains until it is required for processes involved in fertilisation. The function and mechanisms regulating the proteins encoded by many anther-specific genes are not known.

The At39 protein contains a large proportion of lysine (11%), cysteine (13%) and serine (11%). These three amino acids constitute 35% of the protein. However, obvious sequence repeats are not present. A hydropathicity plot revealed the At39 protein contains a hydrophobic region in the first 20 amino acids while the rest of the protein is hydrophilic (FIG. 4B). The hydrophobic region may represent a signal sequence, suggesting the protein is secreted.

On the Genbank database (accession no. AB015475), the At39 gene is categorised as gibberellin-regulated. A BLAST search of the database using the TA39 protein sequence identified a number of other genes also associated with gibberellins. Gibberellin may act as a regulatory factor involved in anther-specific gene expression.

Tissue-specific promoters are important tools for research and may have useful applications in agricultural practices. Such applications include the development of a male sterility system that can be used to breed hybrid crops. Potentially the At39 promoter can be used to regulate gene expression in the anther region of crops such as Canola. To determine if the At39 promoter retains tissue-specificity in other plant species, it must be transformed into other species.

Materials and Methods

1. Seed Surface Sterilization and Germination

Seed were collected, placed in eppendorf tubes and wet with 500 µl of 70% ethanol for 5 minutes. The ethanol was removed and replaced with 500 µl seed sterilization solution (a mixture of bleach, sterile water and 5% SDS at a ratio of 8:15:1 respectively). The tube was shaken and left for 10 minutes at room temperature, and then pulse spun to sediment the seeds. The supernatant was removed, and the seeds were washed four times with sterile water.

Sterilised seeds were grown in 25 mm deep petri dishes containing 50 mL of germination media (GM: 0.5 g MES, 10 g sucrose, 4.6 g Murashige and Skoog Basal Salt mixture, 1 mL 1M KOH, 2 g Phytagel and water to 1 L). Media was autoclaved prior to use, and 1 mL of filter sterilized 1000× vitamin stock added before pouring plates. If selection was required 1 mL of 50 mg/mL kanamycin was also added. Once the seed were sown the plates were sealed with microspore tape and incubated in growth cabinets at 22° C. under constant light.

2. RNA Extraction

RNA extraction was performed following the Progeny Industries DRP$^3$ separation reagent protocol.

Arabidopsis plant tissue was collected, and 100 mg was ground to a fine powder in the presence of liquid nitrogen using a mortar and pestle. The tissue powder was homogenised in 1 mL of DRP$^3$ reagent, and incubated for 5 minutes at room temperature, then transferred to a 1.5 mL eppendorf tube. The sample was suspended in 200 µl chloroform, mixed by vortexing for 20 seconds and incubated for 10 minutes at room temperature. The mixture was separated into phases by centrifugation (Biofuge) (11,300 rpm, 15 minutes at 4° C.). The upper aqueous phase containing the RNA was transferred to a new eppendorf tube, 500 µl of isopropanol was added and the sample was incubated for 5 minutes at room temperature. The RNA was precipitated by centrifugation (11,300 rpm, 8 minutes at 4° C.) and the supernatant was discarded. The RNA pellet was washed in 1 mL of 75% ethanol by vortexing and precipitated by centrifugation (8,800 rpm, 5 minutes at room temperature). The supernatant was removed and the pellet was air dried for 5 minutes before being dissolved in 50 µl water. RNA samples were stored at −20° C.

3. Extraction of Genomic DNA from Plant Tissue Using QIAGEN DNeasy®

The DNA extraction method followed the QIAGEN DNeasy Plant mini kit protocol.

Plant leaves were collected into a 15 mL falcon tube and frozen in liquid nitrogen. The plant tissue (100 mg) was ground to a fine powder in the presence of liquid nitrogen, using a mortar and pestle. The powder was transferred to an eppendorf tube, 400 µl Buffer AP1 and 4 µl RNase A stock solution was added. The suspension was mixed by vortexing and incubated at 65° C. for 10 minutes to lyse the cells. To precipitate unwanted material, 130 µl Buffer AP2 was added. The lysate was mixed and incubated on ice for 5 minutes. The lysate was added to the QIAshredder spin column sitting in a 2 mL collection tube. Without disrupting the pellet the flow-through was transferred to a new eppendorf tube. The total volume was determined, 0.5 volume of Buffer AP3 and 1 volume of 95% ethanol was added and mixed by pipetting. The sample along with any precipitate was place into the DNeasy mini spin column sitting in a collection tube and centrifuged (8000 rpm, 1 minute at room temperature), the flow through was discarded. The column was place into a new collection tube, and 500 µl Buffer AW was added to wash the column. The column was centrifuged (8000 rpm, 1 minute at room temperature) the collection tube was emptied and the wash was repeated as above but was spun for 2 minutes to dry the membrane. The column was transferred to a new eppendorf tube, the DNA was eluted with 100 µl Buffer AE (pre-heated to 65° C.) added directly onto the column membrane. The tube was incubated for 5 minutes at room temperature before centrifugation (8000 rpm, 1 minute at room temperature). The DNA sample was stored at −20° C. until required.

4. Reverse Transcriptase—Polymerase Chain Reaction (RT-PCR)

The two-step RT-PCR procedure was performed using Superscript II RNase reverse transcriptase (GibcoBRL) to synthesise first strand cDNA. The RT reaction mixture was placed in a 0.6 mL thin-walled PCR tube and consisted of 5 µl of 5× First-strand Buffer, 1 µg of template RNA, 30 pmol of Tubulin reverse or Poly (T) primer (PE Biosystems), 1 µl Superscript II, 1 µl of 10 mM dNTP, 2 µl of 0.1M DTT, 1 µl RNase Out inhibitor and sterile water to a total volume of 50 µl. The cDNA was synthesized at 55° C. for 30 minutes in the MJ research minicycler PCR machine.

The cDNA was then used as template DNA in a PCR reaction see below.

5. Polymerase Chain Reaction (PCR)

PCR was initially used to amplify the DNA sequence of interest for use in cloning procedures and later used to verify that the DNA insert had been successfully cloned or transformed into the plant genome. Hence the template DNA used in PCR reactions was either genomic DNA, plasmid DNA isolated by miniprep or a 2 mm² piece of alkali prepared leaf tissue.

The reaction mix was prepared in 0.6 mL thin-walled PCR 15, tubes and consisted of 5 µl of 10×PCR Buffer, 2 µl of 10 mM dNTP's, 3 µl of template DNA, 1 µl of each primer (30 pmol) 1 µl of Taq DNA polymerase and sterile water to total volume of 50 µl. When using a PCR machine without a heat lid, 40 µl mineral oil was added to the surface to prevent evaporation.

The PCR tubes were placed in a MJ Research PCR minicycler and programmed for the following conditions: step 1: 94° C. for 2 minutes, step 2: 55° C. for 30 seconds, step 3: 72° C. for 1-2 minutes, step 4: 94° C. for 30 seconds, step 5: 55° C. for 30 seconds, step 6: 72° C. for 1-2 minutes, step 7: Repeat steps 4-6 for 30 cycles, step 8: 72° C. 10 minutes and finally kept at 4° C. until the reactions were removed from the PCR machine. When the PCR reaction was completed, 10-15 µl of PCR product was run on a 1% agarose gel to confirm the presence of the amplified fragment. The remaining samples were stored at −20° C.

The same basic program was used for all PCR, however there were adjustments made depending on the success of the PCR. The primers tended to have different optimum annealing temperatures (steps 2 and 5) ranging from 50-60° C., although 55° C. was appropriate for most reactions. The extension time also varied depending on the length of the PCR product. Occasionally the number of cycles was increased, but in most cases 30 cycles was adequate.

```
Primers
At39gene-5' (SEQ ID NO: 4)
5' ATGAAATTCCCGGCTGTAAAAGTTCT 3'          (26 mer)

At39gene-3' (SEQ ID NO: 5)
5' AGAAACAAAAGGTATTCACGGACTT 3'           (25 mer)

At39prom-5' (SEQ ID NO: 6)
5' GCACAAGCTTGCTTATAAGCTACTCTTTGCC 3'     (31 mer)

At39prom-3' (SEQ ID NO: 7)
5' TTCCGGATCCGAACTTTTACAGCCGGGAATTT 3'    (32 mer)

Canprom-5' (SEQ ID NO: 8)
5' GCACAAGCTTGTATAGAGTAAATGAGCA 3'        (28 mer)

At39codereg-3' (SEQ ID NO: 9)
5' TTCCGGATCCGGTTGAGAGTATGAACAAAGAA 3'    (32 mer)

NK2 (SEQ ID NO: 10)
5' TTGAGAGCTCGTAGGAACAGAGCAC 3'           (25 mer)

NK1 (SEQ ID NO: 11)
5' CTTGAGCTCGAAGAAATGGGTCGGATTCCATGTT 3'  (34 mer)
```

The restriction sites are shown: BamH1 is underlined, Hind111 is in bold and Sac1 is in italics.

The pair of primers used in the reaction depended on the purpose of the PCR. The At39 gene-specific primers were used to amplify the At39 gene. At39gene-5' binds at position +1 (the ATG translation start site) in the At39 gene, the At39gene-3' primer binds at position +350 in the coding region of the gene, the binding positions are shown in FIG. 4. The At39 promoter-specific primers were used to amplify the At39 promoter region used for cloning, the At39prom-5' primer binds at position −1850 in the 5' promoter region, and the At39prom-3' also binds at position +1 on the complementary strand, the binding positions are represented FIG. 5. The At39-codereg primer binds at position +50 in the coding region of the At39 gene shown in FIG. 4.

6. Testing the Suitability of Primers Used for T-DNA Insertion Screening.

The primers used for screening the T-DNA insertion mutant library were tested under specific PCR conditions that were consistent with those used at the University of Wisconsin-Madison Knockout Facility.

The PCR reaction was performed according to the conditions outlined by the KO facility using TaKaRa Ex-Taq™. The PCR reaction included 4 µl 10× Ex-taq buffer, 4 µl dNTP, 1 µl of each primer (12 pmol), 2 µl Arabidopsis genomic DNA (ecotype WS) and water to a total volume of 40 µl. The samples were placed in the PCR machine (MJ research minicycler) and heated to 96° C. for a hot start, before 10 µl of hot start enzyme mix was added. The hot start mix consisted of 8.5 µl water, 1 µl Ex-taq buffer and 0.5 µl Ex-taq polymerase. After the mix was added the PCR program continued with 36 cycles of 94° C. for 15 seconds, 65° C. for 30 seconds and 72° C. for 2 minutes, followed by a final extension time of 72° C. for 4 minutes then kept at 4° C. until removed from the machine.

Four reactions were performed using different primer combinations, 1) Con-1A+Con-1B provided a standard to compare the effectiveness of the gene specific primers 2) Con-1A+Con-1B+JL-202 tested the compatibility of the control primers with the T-DNA left border primer 3) Scrn103-5'+Scrn103-3' tested the suitability of the AtMYB103 gene specific primers 4) Scrn103-5'+Scrn103-3'+JL202 tested the compatibility of the gene specific primers with the T-DNA border primer.

```
Primers
SEQ ID NO: 12-Con-1A:
5' CGTCTAGGTGGTTCAGTACCTGTTGAATG 3'   (29 mer)

SEQ ID NO: 13-Con-1B:
5' TTTATCGAAGAAACATGTCGTTGAACCAG 3'   (29 mer)

SEQ ID NO: 14-JL-202:
5' CATTTTATAATAACGCTGCGCACATCTAC 3'   (29 mer)

SEQ ID NO: 15-Scrn103-5'
5' GGCTAGTTTGTTATCCAAGTCGTTCTACC 3'   (29 mer)

SEQ ID NO: 16-Scrn103-3'
5' AGTTTTGTGTATGCGTTCAATAACCTTT 3'    (28 mer)
```

7. DNA Fragment Isolation using UltraClean™ 15

DNA fragments were isolated following the Mo Bio Laboratories UltraClean15 protocol.

The required DNA fragment or PCR product was run on a 1% agarose gel. Using a razor blade the desired band was cut from the gel and place into an eppendorf tube. The weight of the gel band was determined, 0.5 volume of Ultra TBE Melt and 4.5 volumes of Ultra Salt was added. The tube was incubated at 55° C. for 5 minutes or until the gel melted. The Ultra Bind was vortexed until homogenous then 6 µl was added to the solution. The mixture was incubated for 5 minutes at room temperature, and mixed several times during the incubation. The solution was briefly centrifuged (13,000 rpm 5 seconds at room temperature) and the supernatant was discarded. The pellet was washed with 1 mL of Ultra Wash solution by vortexing, and then centrifuged (13,000 rpm, 5 seconds at room temperature). All traces of the supernatant were removed by pippetting. The pellet was resuspended in 15 µl of water and incubated for 10 minutes. The suspension was centrifuged (13,000 rpm, 1 minute at room temperature) and the DNA was transferred to a new tube, and stored at −20° C.

8. Sequence Analysis-Big Dye Terminator

The sequencing reactions were performed using the Big Dye Terminator Cycle sequencing ready reaction kit manufactured by PE Applied Biosystems.

The sequencing reaction consisted of 6 µl of Terminator Ready Reaction Mix, 100-500 ng of template DNA, 3.2 pmol of primer and sterile water to a total volume of 20 µl. The reagents were placed in a 0.6 mL thin-walled PCR tube and mixed well. The tubes were placed in the thermal cycler PCR machine (MJ research minicycler). The program was set for the required conditions, step 1: 96° C. for 30 seconds, step 2: 50° C. for 15 seconds, step 3: 60° C. for 4 minutes, step 4: repeated steps 1-3 for 25 cycles and finally held at 4° C. until the samples were removed.

The sequencing reaction product was purified using ethanol precipitation. The reaction mixture was transferred to an eppendorf tube containing 2.0 µl 3M sodium acetate and 40 µl of 95% ethanol. The contents of the tube were vortexed and place in −80° C. freezer for 20 minutes. The DNA was precipitated by centrifugation (13,000 rpm, 15 minutes at 4° C.), and the supernatant was removed. The pellet was washed with 200 µl 70% ethanol, then vortexed and centrifuged (13,000 rpm, 10 minutes at 4° C.). The supernatant was removed by pippetting and the pellet was dried under vacuum in a Speedvac concentrator for 10 minutes. The sample was sent to the Microbiology Department at Monash University, Clayton for automated sequencing.

9. Preparation of *E. coli* Competent Cells

*E. coli* cells (DH5α) were plated on 2YT plates without antibiotics and incubated overnight at 37° C. A single colony was used to inoculate a 15 mL 2YT culture in a falcon tube and grown overnight at 37° C. orbital shaker. The cells were collected by centrifugation (Interfuge) (3000 g, 15 minutes at room temperature), and the supernatant was discarded. The cells were resuspended with 1 mL of sterile ice-cold water and transferred to an eppendorf tube. The cells were centrifuged (Biofuge) (13,000 rpm, 7 minutes at 4° C.), the supernatant was discarded and the pellet was resuspended in 1 mL ice-cold water, this process was repeated three times. Then the cells were centrifuged (13,000 rpm, 5 minutes at 4° C.), the supernatant was discarded. The cells were resuspended in 1 mL of ice-cold 10% glycerol, and harvested by centrifugation (13,000 rpm, 3 minutes at 4° C.). The supernatant was removed and finally the cells were resuspended in 500 µl ice cold 10% glycerol. The cell suspension was transferred to eppendorf tubes in 50 µl aliquots, snap frozen in liquid nitrogen and stored at −70° C.

10. Restriction Digestion

To prepare various vectors and DNA inserts for cloning, a number of restriction digest were performed, using a number of restriction enzymes (Boehringer-Mannheim) depending on the application and type of DNA or plasmid used in the reaction.

The digestion reaction contained the DNA of interest, 1 µl of each restriction enzyme (Boehringer-Mannheim), 2 µl of the corresponding restriction buffer and sterile water up to a total volume of 20 µl. The reaction was incubated at 37° C. for 1-2 hours, and the entire reaction was run on a 1% agarose gel and then isolated using the UltraClean15 kit (4.7). A small portion of the digested DNA was run on a 1% agarose gel to visualize the amount of DNA recovered to determine the amount required for ligation.

Dephosphorylation:

The pB4.1.21 vector was kindly supplied by Trudi Higginson. This vector was digested with Sac1 as above, but was dephosphorylated to reduce self-ligation. The dephosphorylation reaction was performed immediately after the restriction digest was incubated so that the DNA only needed to be isolated from the gel once, to reduce the amount of DNA lost during the purification process. Dephosphorylation was achieved by adding 1 µl of calf intestinal phosphatase (CIP) (Boehringer-Mannheim) and 2 µl of 10×CIP buffer to the digest reaction and incubated at 37° C. for 30 minutes. The reaction was then run on a 1% gel and isolated as above.

Blunt-ending:

PCR amplified products were blunt ended before cloning into the pPRscript cloning vector, since A-overhangs on the PCR product can interfere with cloning. In the reaction 1 µl of T4 polymerase buffer and 1 µl T4 DNA polymerase (Promega) was added to the purified PCR product and incubated at 37° C. for 30 minutes. The insert DNA was then used in a ligation reaction as described below.

11. Ligations

A large number of ligations were performed to clone insert DNA into vectors. The volume of vector and insert DNA varied in each reaction depending of the amount visualised after isolation from the restriction digest, usually a 2-3 fold excess of insert DNA was present compared to the amount of vector DNA. The vector and insert DNA were added to an eppendorf tube containing 1 µl of 10× ligation buffer (Promega) and 1 U T4 DNA ligase (Promega) along with sterile $H_2O$ to a total volume of 10 µl. Ligations were incubated at room temperature overnight.

In some instances the 10× ligation buffer was replaced with 5 µl of 2× rapid ligase buffer (Promega) and the total volume was increased to 15 µl, the ligation reaction was incubated at room temperature for 10 minutes.

Ligations were used immediately for transformation or stored at −20° C.

QIAGEN PCR Cloning Kit Ligation

Ligations involving the pDrive cloning kit were performed under the conditions specified by QIAGEN to ensure optimal results. The ligation reaction mixture consisted of 1 µl pDrive cloning vector (50 ng/µl), 2 µl PCR product (non-purified), 5 µl ligation master mix and distilled water to a total volume of 10 µl. The mixture was incubated at 16° C. in a water bath for 2 hours. The ligation mixture was used immediately or stored at −20° C.

12. Transformation of *E. coli* Competent Cells

A 50 µl aliquot of electro-competent *E. coli* (DH5α) cells were thawed on ice, and 2 µl of ligated plasmid (4.11) was added. This mixture was mixed by pippetting, and then left on ice for 1 minute. The cell mixture was transferred to an ice-cold 0.1 cm electroporation curvette, and tapped gently to remove any air bubble. The outside of the curvette was wiped dry with a tissue and placed into the electroporator (BIORAD micropulser), the program was set for Eco1. An electric shock (1.8 kV) pulse was applied to the cells. Immediately 100 µl of ice-cold 2YT medium was added to the curvette. The suspension was transferred to an eppendorf tube and placed in the 37° C. incubator for 1 hour. The cells were spread onto 2YT plates containing the appropriate antibiotic to select for cells containing the transformed plasmid. The plates were incubated at 37° C. overnight.

Blue-white Screening

In addition to antibiotic selection, blue/white colony selection was also used for pBluescript and pDrive vectors to assist in the identification of positive colonies. For blue/white screening, 20 µl of 50 mg/mL X-Gal (5-bromo-4-chloro-3-indolyl-β-D-galactopyranoside) was spread onto the plates and allowed to dry before the plating transformed cells.

13. Plasmid DNA Miniprep

A single bacterial colony from a transformation plate was used to inoculate 15 mL of 2YT medium containing the correct antibiotic to select for the plasmid. The bacterial cultures were grown overnight at 37° C. in an orbital shaker.

The culture was transferred to an eppendorf tube and centrifuged (13,000 rpm, 2 minutes at room temperature) the supernatant was discarded. This process was repeated until 5 mL of culture was used. The bacterial cells were resuspended in 200 µl of Resuspension solution by vortexing. To lyse the cells, 200 µl of Cell lysis solution was added. After mixing, 200 µl of neutralisation solution was added, the sample was mixed before centrifugation (13,000 rpm, 7 minutes at room temperature). The supernatant was transferred to a new eppendorf tube containing 1 mL of DNA purification resin. The solution was added to the minicolumn barrel and a vacuum was applied drawing the solution through the minicolumn. Applying 2 mL of column wash to the minicolumn washed the plasmid DNA. The minicolumn was placed into an eppendorf tube and briefly pulse spun to dry the resin and remove any residual column wash. The minicolumn was transferred to a new eppendorf tube and 50 µl of water was added, after incubation for 10 minutes at room temperature, the DNA was eluted by centrifugation (10,000 rpm, 1 minute at room temperature). The minicolumn was removed and the plasmid DNA is stored at −20° C. Adapted from Promega technical bulletin protocol.

14. Transformation of *Agrobacterium tumefaciens* Electro-competent Cells

A 50 µl aliquot of electro-competent *Agrobacterium* (GV3101) cells was thawed on ice. The pBI binary vector containing the insert was isolated and purified with miniprep (see 12), 2 µl of plasmid DNA was added to the thawed cells and incubated on ice for 1 minute. The sample was transferred to a 0.1 cm ice-cold curvette ensuring no air bubbles were present. The outside of the curvette was wiped dry with a tissue and placed into the electroporation machine (BIORAD micropulser). The program was set for AGR and an electric pulse (2.2 kV) was applied to the bacterial cells. Immediately 100 µl of 2YT broth was added to the curvette and gently mixed. The suspension was transferred to an eppendorf tube and incubated at 25° C. for 2 hours. The cells were spread onto 2YT plates containing kanamycin, gentamycin, and rifampicin antibiotics to select for the plasmid. The plates were incubated at 25° C. for two days until the *Agrobacterium* grew.

15. Genetic Transformation of *Arabidopsis thaliana*

Wildtype *Arabidopsis thaliana* (Columbia) seeds were sown in punnets containing potting mix. The potting mix was held in place with plastic mesh secured by rubber bands. Plants were grown at 20° C. with a 24 hour day cycle until they were ready for transformation. When the plants were beginning to flower the bolts were removed to encourage secondary shoots to increase the number of florets.

Colonies from *A. tumefaciens* (GV3101) transformed with the binary vector containing the gene of interest were used to inoculate 10 mL 2YT broth containing 50 µg/mL rifampicin, 25 µg/mL gentamycin and 50 µg/mL kanamycin. The cells were grown overnight at 25° C. in an orbital shaker. When thick, 3 mL was used to inoculate 300 mL 2YT broth containing 50 µg/mL kanamycin and 25 µg/mL gentamycin in a 1 liter flask. The culture was grown overnight at 25° C. in an orbital shaker. The culture was transferred into two 250 mL centrifuge bottles and centrifuged using a HS4 rotor Sorval RC) (5000 rpm, 15 minutes at room temperature). The supernatant was discarded and the pellet was resuspended in 200 mL of infiltration media (2.3 g Murashiage and Skoog Basal Salt mixture, 1 mL of 1000× vitamin stock, 50 g sucrose, 100 µl of 100 µg/mL BAP and 1 mL Silwet). The suspension was poured into a container, which was placed into the vacuum desiccator. The pots of Arabidopsis plants were saturated with water prior to the transformation to prevent the *Agrobacterium* absorbing into the soil.

The pots were placed upside down into the *Agrobacterium* solution in the container. The plants were place under vacuum in the desiccator for 5 minutes, during this time the desiccator was periodically tapped to remove any air bubbles trapped amongst the plants. The vacuum was released quickly and the pots were removed and left on their side to drain for 5 minutes. The pots were placed upright into a plastic tub covered in paper towel, and placed in the dark for 24 hours. The plants were uncovered and placed under constant illumination until the seeds were ready to harvest. The seeds were sterilized and germinated on growth medium containing 50 µg/mL kanamycin (see 2).

16. Alkali Plant Tissue Preparation

Transformed plants with kanamycin resistance underwent PCR analysis to determine if the plant is transgenic. The plant tissue was prepared for PCR reactions following the protocol published by Klimkuk et al., (1993) Plant Journal 3:493-494.

A leaf from kanamycin resistant seedlings were collected and cut into small pieces (2 mm$^2$) with a sterile razor blade. The tissue pieces were placed into a 1.5 mL eppendorf tube containing 40 µl of 0.25 M NaOH and boiled at 100° C. for 1 minute in a water bath. The samples were neutralized with 40 µl 0.25 M HCl and 20 µl 0.5 M Tris-HCl (pH 8.0), and boiled for a further 2 minutes. A piece of the leaf was transferred to a 0.6 mL PCR tube and analysed with PCR reactions (see 5).

17. β-Glucuronidase (GUS) Staining

Tissues samples from transgenic plants were placed into an 1.5 mL eppendorf tube and submersed in X-gluc solution (0.5 mg/mL X-gluc in dimethylformamide, 50 mM NaPO$_4$, pH 7 and 0.05% Triton X-100). The samples were incubated at 37° C. for several hours or overnight. The X-gluc solution was removed and replaced with 70% ethanol. The samples were incubated at room temperature for several hours or until the tissue was void of chlorophyll. The GUS expression pattern was analysed with light microscopy and photographed.

18. Southern Blotting onto a Nylon Membrane

The PCR products obtained from the University of Wisconsin-Madison Knockout Facility were run on a 1.0% agarose gel and photographed with a ruler beside the gel to identify band positions later on.

The gel was rinsed in distilled water and placed into a glass dish containing 500 mL denaturation solution (1.5 M NaCl, 0.5 M NaOH) to make the DNA molecules single stranded. The dish was placed onto a platform rocker to shake for 20 minutes, the solution was replaced with a equal volume of fresh denaturation solution and shaken a further 20 minutes. The denaturation solution was removed. The gel was rinsed in distilled water, and 500 mL of neutralisation solution (1.5 M NaCl, 0.5 M Tris pH 7.0) was added to the dish and left to shake a further 20 minutes. The solution was replaced with fresh neutralization solution and shaken a further 20 minutes.

The transferred pyramid was set up by placing a glass sheet across top of a plastic container partially filled with 20×SSC transfer buffer (3M NaCl, 0.3M Na$_3$ citrate.2H$_2$O). The wick consisted of three lengths of 3 mm whatman paper placed over the top of the glass plate extending over the edges down into the transfer buffer. The gel was placed onto the wick and air bubbles were removed by rolling a glass rod over the gel. Strips of glad wrap were placed around the edges of the gel to ensure the transfer buffer flowed through the gel rather than around it. A piece of Amersham Hybond-N nylon membrane was cut to the size of the gel. The nylon membrane was place onto the gel with forceps to avoid touching the membrane. The top left hand corner was cut off the membrane to remember the orientation of the gel. Air bubbles were removed by rolling a glass pipette over the surface. Five sheets of whatman paper cut to the same size as the nylon membrane were soaked in 20×SSC and placed onto of the nylon membrane. A stacked of paper towel approximately 10 cm high were place on top. Finally a glass plate and a weight were placed on top to keep everything in place. The transfer was left to proceed overnight.

The transfer pyramid was dismantled. The paper towel and filter papers were removed. A pencil was used to mark the position of the wells. The nylon membrane was removed and washed in 2×SSC to remove any agarose for 1 minute. The membrane was place on a sheet of filter paper to dry before being cross-linked in the Stratagene UV Stratalinker 2400, this allows the membrane to be probed several times. The membrane was sealed in plastic wrap and stored at 4° C. until probed.

19. Labeling $^{32}$P Probe Using BIO-RAD Megaprime Kit

The probe was amplified using the PCR conditions and the specific primers described in 4.6 and isolated from a gel using the Ultraclean kit (see 7 materials and methods).

After the DNA was isolated, 25 ng of template DNA was denatured at 95° C. for 5 minutes. At room temperature 10 µl labeling buffer, 5 µl reaction buffer, 2 µl enzyme and distilled water to a total volume of 50 µl was added. The tube was well mixed and pulse spun in a micro-centrifuge to bring the content to the bottom of the tube. The radio-labeled dNTP, 5 µl [α-$^{32}$P] dCTP activity 3000 Ci/mmol was added and mixed by pippetting The tube was incubated at 37° C. for 10 minutes, then 5 µl 0.2 M EDTA was added to stop the reaction.

The NICK® Spin Column was used to remove the unincorporated $^{32}$P-nucleotides. The column was inverted several times to re-suspend the gel the caps were removed to drain the column. The column was rinsed with 2 mL water and allowed to drain. The column was placed into a centrifuge tube and centrifuged (500×g, 4 minutes at room temperature), the contents of the tube was discarded. A 0.6 mL PCR tube was placed at the bottom of the centrifuge tube, ensuring the tip of the column is placed inside the PCR tube. The nick-translated sample was applied to the gel surface inside the column, and eluted by centrifugation (500×g, 4 minutes at room temperature). The column was discarded and the PCR tube containing the purified probe was removed and stored at −20° C. until required for hybridization.

20. Hybridisation Analysis of Southern Blot

The nylon membranes were wet with 6×SSC. The membranes were rolled up and placed into a hybridization tube containing 40 mL aqueous pre-hybridisation/hybridisation (APH) solution. The tube was placed into a hybridization oven (Mini Oven MKII) and incubated with rotation for 3 hours at 68° C. To prepare for hybridisation, the probe was denatured in a 100° C. water bath for 10 minutes and then place on ice.

After pre-hybridisation the APH solution was removed from the hybridisation tube and replaced with the same volume of APH solution pre-warmed to 68° C. The denatured probe was added and the tube was place back into the hybridisation oven and incubated with rotation at 68° C. overnight.

After hybridization the APH solution was removed and disposed of into radioactive waste container. The membranes were then subjected to a series of washes at increasing levels of stringency. First 100 mL of 2×SSC/0.1% SDS solution was added to the tube and incubated with rotation at room temperature for 10 minutes, the solution was replaced and incubated a further 10 minutes.

This solution was removed and replaced with 100 mL 0.2×SSC/0.1% SDS and incubated with rotation for 10 minutes. The solution was changed, repeating the incubation. For a moderate stringency wash the solution was replaced with 100 mL 0.2×SSC/0.1% SDS solution pre-warmed to 42° C., and a further two washes were repeated as described.

The radioactivity level was monitored with a gieger counter throughout the washing process. If the radioactivity was still high a final high stringency wash was performed. The membranes were removed from the tube and placed into a glass-baking dish and covered with 0.1×SSC/0.1% SDS solution pre-warmed to 68° C. The container was placed into a 68° C. water-bath with shaker and incubated for 15 minutes.

The final wash solution was removed and the membranes were rinsed with 2×SSC and wrapped in plastic wrap.

In the darkroom, the membranes were placed into a cassette with a piece of autoradiograph film placed on top. The cassette was closed and placed into a black plastic bag and stored at −80° C. for two nights.

The cassette was removed from the freezer and allowed to return to room temperature. The autoradiograph film was developed in the dark room by submersing the film in to developing fluid for 5 minutes. The film was rinsed in water then submersed in fixative solution for 5 minutes. The film was rinsed in running water for 5 minutes then left to dry.

The claims defining the invention are as follows:

1. An expression cassette comprising a functional anther specific promoter comprising:
   (a) the nucleotide sequence of SEQ ID NO: 1; or
   (b) a functional fragment of SEQ ID NO: 1, wherein said fragment is capable of directing expression of a heterologous nucleic acid molecule to which it is operably linked, in anther and/or pollen tissue of a plant transformed with the expression cassette;
   and wherein the expression cassette further comprises a site for inserting the heterologous nucleic acid molecule, such that the heterologous nucleic acid molecule would be operably linked to the promoter and would be specifically expressed in anther and/or pollen tissue of a plant transformed with the expression cassette.

2. A recombinant plasmid comprising
   (i) a functional anther specific promoter comprising:
      (a) the nucleotide sequence of SEQ ID NO: 1; or
      (b) a functional fragment of SEQ ID NO: 1, wherein said fragment is capable of directing expression of a heterologous nucleic acid molecule to which it is operably linked, in anther and/or pollen tissue of a plant transformed with the plasmid;
   and wherein the plasmid further comprises a site for inserting the heterologous nucleic acid molecule, such that the heterologous nucleic acid molecule would be operably linked to the promoter and would be specifically expressed in anther and/or pollen tissue of a plant transformed with the plasmid; or
   (ii) the expression cassette of claim 1.

3. A plant cell or cell line transformed with:
   (i) a functional isolated anther specific promoter comprising:
      (a) the nucleotide sequence of SEQ ID NO: 1; or
      (b) a functional fragment of SEQ ID NO: 1, wherein said fragment is capable of directing expression of a heterologous nucleic acid molecule to which it is operably linked, in anther and/or pollen tissue of a plant transformed with the promoter;
      and wherein the promoter further optionally comprises a heterologous nucleic acid molecule operably linked to the promoter; or
   (ii) the expression cassette of claim 1; or
   (iii) the recombinant plasmid of claim 2.

4. A transgenic plant comprising the transformed cell of claim 3.

5. Propagation material comprising the transformed cell of claim 3.

6. The propagation material of claim 5, including one or more of a fruit, seed, tuber, root-stock, seedling, or a cutting.

7. The expression cassette of claim 1, wherein the heterologous nucleic acid molecule inhibits the formation of anthers and/or pollen, and/or imparts resistance to environmental stress.

8. The expression cassette of claim 7, wherein the environmental stress is one or more of temperature extreme, salinity, pests, or infection.

9. The recombinant plasmid of claim 2, wherein the heterologous nucleic acid molecule inhibits the formation of anthers and/or pollen, and/or imparts resistance to environmental stress.

10. The recombinant plasmid of claim 9, wherein the environmental stress is one or more of temperature extreme, salinity, pests, or infection.

11. The plant cell of claim 3, wherein the heterologous nucleic acid molecule inhibits the formation of anthers and/or pollen, and/or imparts resistance to environmental stress.

12. The plant cell of claim 11, wherein the environmental stress is one or more of temperature extreme, salinity, pests, or infection.

13. The transgenic plant of claim 4, wherein the heterologous nucleic acid molecule inhibits the formation of anthers and/or pollen, and/or imparts resistance to environmental stress.

14. The transgenic plant of claim 13, wherein the environmental stress is one or more of temperature extreme, salinity, pests, or infection.

15. The propagation material of to claim 5, wherein the heterologous nucleic acid molecule inhibits the formation of anthers and/or pollen, and/or imparts resistance to environmental stress.

16. The propagation material of claim 15, wherein the environmental stress is one or more of temperature extreme, salinity, pests, or infection.

17. The expression cassette of claim 1, further comprising a heterologous nucleic acid molecule operably linked to the promoter.

18. The recombinant plasmid of claim 2, further comprising a heterologous nucleic acid molecule operably linked to the promoter.

19. A method for introducing into a plant a heterologous nucleic acid molecule which is to be specifically expressed in anthers and/or pollen, the method comprising the steps of:

(a) transforming a plant cell with the expression cassette of claim 1 or the recombinant plasmid of claim 2; and
(b) regenerating the plant from the transformed plant cell.

20. A method of specifically expressing a heterologous nucleic acid molecule in anther and/or pollen of a plant, the method comprising the steps of:

(a) transforming a plant cell with the expression cassette of claim 17 or the recombinant plasmid of claim 18; and
(b) regenerating the plant from the plant cell.

* * * * *

SEQUENCE LISTING

```
<160> NUMBER OF SEQ ID NOS: 25

<210> SEQ ID NO 1
<211> LENGTH: 1860
<212> TYPE: DNA
<213> ORGANISM: Arabidopsis thaliana

<400> SEQUENCE: 1
gcacaagctt gcttataagc tactctttgc caacaaattc gcaacaatga tttctagaac      60
tataatcagt tgatggggga agaaaatgtt gaaagttgta caatgaatca agttaaagtt     120
aaaatacttt tttcccgatt ctctgcaggt tacatatatg tgtatataca cagtatgtga     180
atgatcaaaa agaagattta atatatctaa gcatgcagac aaaaacctat tgctaaaaag     240
atttctaaga accggagacc gtttaccaaa caaaatatga agttgaattc atcccatttg     300
tcactcgatt agacaagatt cgtcgaacga agatatctat taacgatcta ctaactttag     360
ttaaatcgtg acaaaacaca catcattcat atttgatagt gaataagtcg gtggtccatc     420
gttttaactt tgattgatat ccttaaaatt gatgcatagc tttaaacaac caatactttc     480
ttatggattg tttttcttcc aacttctcta agggttttat tttagaaaat tgattataag     540
tattaaatga aatctaagag aaaaaaaaaa aaaaaagag gagaaagatg agaagttccc     600
atgcctttag attcggatta cgtgtgtcac tcttttttata gctttaacgc gatggtcgct     660
caacgtgaac gacattgtcc cactaagaaa ataatgatc atttcatgtg tatttttct     720 ttatcaaatt tttaaattat atatacatat ctaactttga taacaacaac aagaatctgt     780
aatacaatta tacaacggca cgcaaacagc agaattagta gatattcttt aaagcaaatt     840
taccatattt gtaacatttc tattagtatg atatgataca aaagtttgga acatgatttg     900
atagaagcta acgtcaattc catttctttta ataaatggta aaaggtatat aaacagagta     960
ttagtcctca aaaacattgt aaacatattg ttttaaaaca atttaccagt atatattgac    1020
aatagtttaa ctgaattgac gtgcaagtca atattattac cttattaggg ggcgttattg    1080
gttcttaatt tacaaggaat ttagatgatt tcaatcacat tctataaagt attttaaagt    1140
attgttagag agttttttat aatcttgttg attagttttt cataattttg taaagttttt    1200
caaacaatct ctctatttta ataatacttt tcatgactttt ccatgacttt attttgtgaa    1260
gaaaaatgta aaaagtcatg aaccaataac ataataattg aaatcattaa caatgagaaa    1320 ttttttttgtt ttaattgaat aacacaaaac ttttaatgac ttgagtatga atccaataac    1380
ccaaaattta tgcagatttt agaatacttc ttataaatct taaatgaata acacaaaact    1440
ttaacatact tttaacaaat cttgattgaa taacaacaga ttctacatga cattttaaat    1500
cactaaaact cttttgaaat cataaaccaa taacaacccc ttagtttttt actatttgaa    1560
ttctgacgta ctttttttatt agttgaattt ctataaatga gaaaacatta attatttctt    1620
aatctttgaa cttaagcccc acaaaaatct tataaattgg gacagatgga ctagataaca    1680
agcgtttcac ctactccaaa atttccctat aagtaactct ttttgtaacc tcctttttctt    1740 cccaaaccat cactccttttt gcattgtgtg aaaccttcga gttttctctt catcttctca    1800
```
aagtaacaaa ctttctccaa acagattatt attaaaacaa tctcatcaag aactacgatg    1860

<210> SEQ ID NO 2
<211> LENGTH: 89
<212> TYPE: PRT
<213> ORGANISM: Arabidopsis thaliana

<400> SEQUENCE: 2

Met Lys Phe Pro Ala Val Lys Val Leu Ile Ile Ser Leu Leu Ile Thr
1               5                   10                  15

Ser Leu Phe Ile Leu Ser Thr Ala Asp Ser Ser Pro Cys Gly Gly
            20                  25                  30

Lys Cys Asn Val Arg Cys Ser Lys Ala Gly Arg Gln Asp Arg Cys Leu
        35                  40                  45

Lys Tyr Cys Asn Ile Cys Cys Glu Lys Cys Asn Tyr Cys Val Pro Ser
50                  55                  60

Gly Thr Tyr Gly Asn Lys Asp Glu Cys Pro Cys Tyr Arg Asp Met Lys
65                  70                  75                  80

Asn Ser Lys Gly Thr Ser Lys Cys Pro
                85

<210> SEQ ID NO 3
<211> LENGTH: 74
<212> TYPE: PRT
<213> ORGANISM: Nicotiana tabacum

<400> SEQUENCE: 3

Ile His Val Leu Ala Leu Leu Leu Ile Phe Ala Ser Thr Lys Ile
1               5                   10                  15

His His Ala Gln Gly Lys Ser Ile Thr Gly Pro Cys Val Val Ala Cys
            20                  25                  30

Ser Lys Lys Thr Ile Ala Cys Val Val Arg Cys Arg Phe Ala Thr Asp
        35                  40                  45

Lys Cys Ser Gln Asp Cys Ala Ile Asp Ser Ile His Cys Val Ser Ser
    50                  55                  60

Cys Leu Leu Gln Asn Ser Ser Ser Pro Pro
65                  70

<210> SEQ ID NO 4
<211> LENGTH: 26
<212> TYPE: DNA
<213> ORGANISM: Artificial
<220> FEATURE:
<223> OTHER INFORMATION: Synthetic oligonucleotide primer

<400> SEQUENCE: 4
atgaaattcc cggctgtaaa agttct                                            26

<210> SEQ ID NO 5
<211> LENGTH: 25
<212> TYPE: DNA
<213> ORGANISM: Artificial
<220> FEATURE:
<223> OTHER INFORMATION: Synthetic oligonucleotide primer

<400> SEQUENCE: 5
agaaacaaaa ggtattcacg gactt                                             25

<210> SEQ ID NO 6
<211> LENGTH: 31
<212> TYPE: DNA
<213> ORGANISM: Artificial

```
<220> FEATURE:
<223> OTHER INFORMATION: Synthetic oligonucleotide primer

<400> SEQUENCE: 6
gcacaagctt gcttataagc tactctttgc c                              31

<210> SEQ ID NO 7
<211> LENGTH: 32
<212> TYPE: DNA
<213> ORGANISM: Artificial
<220> FEATURE:
<223> OTHER INFORMATION: Synthetic oligonucleotide primer

<400> SEQUENCE: 7
ttccggatcc gaacttttac agccgggaat tt                             32

<210> SEQ ID NO 8
<211> LENGTH: 28
<212> TYPE: DNA
<213> ORGANISM: Artificial
<220> FEATURE:
<223> OTHER INFORMATION: Synthetic oligonucleotide primer

<400> SEQUENCE: 8
gcacaagctt gtatagagta aatgagca                                  28

<210> SEQ ID NO 9
<211> LENGTH: 32
<212> TYPE: DNA
<213> ORGANISM: Artificial
<220> FEATURE:
<223> OTHER INFORMATION: Synthetic oligonucleotide primer

<400> SEQUENCE: 9
ttccggatcc ggttgagagt atgaacaaag aa                             32

<210> SEQ ID NO 10
<211> LENGTH: 25
<212> TYPE: DNA
<213> ORGANISM: Artificial
<220> FEATURE:
<223> OTHER INFORMATION: Synthetic oligonucleotide primer

<400> SEQUENCE: 10
ttgagagctc gtaggaacag agcac                                     25

<210> SEQ ID NO 11
<211> LENGTH: 34
<212> TYPE: DNA
<213> ORGANISM: Artificial
<220> FEATURE:
<223> OTHER INFORMATION: Synthetic oligonucleotide primer

<400> SEQUENCE: 11
cttgagctcg aagaaatggg tcggattcca tgtt                           34

<210> SEQ ID NO 12
<211> LENGTH: 307
<212> TYPE: DNA
<213> ORGANISM: Triticum aestivum

<400> SEQUENCE: 12
atgaagaagc ttcgcaccac cactgccacc accactctcg ctctcattct cctcctcgtc    60
ctcatagcag ccacgtccct ccgtgtcgcc atggctggat cagcgttctg cgacagcaag   120
tgcggggtga ggtgctccaa gacgggccgg cacgacgact gcctcaagta ctgcgggata   180
```

```
tgctgcgccg agtgcaactg cgtgccgtcg gggacagccg gcaacaagga cgagtgcccc    240
tgctaccgcg acaagaccac cggccacggc gcgcgcacga ggcccaagtg cccatgatcc    300
gccacca                                                               307
```

<210> SEQ ID NO 13
<211> LENGTH: 98
<212> TYPE: PRT
<213> ORGANISM: Triticum aestivum

<400> SEQUENCE: 13

```
Met Lys Lys Leu Arg Thr Thr Thr Ala Thr Thr Leu Ala Leu Ile
1               5                   10                  15

Leu Leu Leu Val Leu Ile Ala Ala Thr Ser Leu Arg Val Ala Met Ala
            20                  25                  30

Gly Ser Ala Phe Cys Asp Ser Lys Cys Gly Val Arg Cys Ser Lys Thr
        35                  40                  45

Gly Arg His Asp Asp Cys Leu Lys Tyr Cys Gly Ile Cys Cys Ala Glu
    50                  55                  60

Cys Asn Cys Val Pro Ser Gly Thr Ala Gly Asn Lys Asp Glu Cys Pro
65                  70                  75                  80

Cys Tyr Arg Asp Lys Thr Thr Gly His Gly Ala Arg Thr Arg Pro Lys
                85                  90                  95

Cys Pro
```

<210> SEQ ID NO 14
<211> LENGTH: 23
<212> TYPE: DNA
<213> ORGANISM: Artificial
<220> FEATURE:
<223> OTHER INFORMATION: Synthetic oligonucleotide primer

<400> SEQUENCE: 14

```
tgcaactgcg tgccgtcggg gac                                             23
```

<210> SEQ ID NO 15
<211> LENGTH: 24
<212> TYPE: DNA
<213> ORGANISM: Artificial
<220> FEATURE:
<223> OTHER INFORMATION: Synthetic oligonucleotide primer

<400> SEQUENCE: 15

```
aacaaggacg agtgcccctg ctac                                            24
```

<210> SEQ ID NO 16
<211> LENGTH: 366
<212> TYPE: DNA
<213> ORGANISM: Arabidopsis thaliana

<400> SEQUENCE: 16

```
atgaaattcc cggctgtaaa agttcttatt atctctcttc tcatcacatc ttctttgttc    60
atactctcaa ccgcggattc gtgtaagtat acacaatgca ttttcttatt ttagatactt   120
ttctcattag aaatttagct ttcttaataa aattgtattg tgatgatgga ttaattagca   180
ccatgcggag gaaatgcaa cgtgagatgt tcaaaggcag aagacaaga taggtgtctc    240 aagtattgta atatatgttt cgagaagtgt aactattgtg ttccttcagg cacttatgga   300
aacaaagatg aatgcccttg ttaccgcgat atgaagaact ccaaaggcac gttcaaatgt   360
ccttga                                                               366
```

<210> SEQ ID NO 17
<211> LENGTH: 29
<212> TYPE: DNA
<213> ORGANISM: Artificial
<220> FEATURE:
<223> OTHER INFORMATION: Synthetic oligonucleotide primer

<400> SEQUENCE: 17
cgtctaggtg gttcagtacc tgttgaatg                              29

<210> SEQ ID NO 18
<211> LENGTH: 29
<212> TYPE: DNA
<213> ORGANISM: Artificial
<220> FEATURE:
<223> OTHER INFORMATION: Synthetic oligonucleotide primer

<400> SEQUENCE: 18
tttatcgaag aaacatgtcg ttgaaccag                              29

<210> SEQ ID NO 19
<211> LENGTH: 29
<212> TYPE: DNA
<213> ORGANISM: Artificial
<220> FEATURE:
<223> OTHER INFORMATION: Synthetic oligonucleotide primer

<400> SEQUENCE: 19
cattttataa taacgctgcg cacatctac                              29

<210> SEQ ID NO 20
<211> LENGTH: 29
<212> TYPE: DNA
<213> ORGANISM: Artificial
<220> FEATURE:
<223> OTHER INFORMATION: Synthetic oligonucleotide primer

<400> SEQUENCE: 20
ggctagtttg ttatccaagt cgttctacc                              29

<210> SEQ ID NO 21
<211> LENGTH: 28
<212> TYPE: DNA
<213> ORGANISM: Artificial
<220> FEATURE:
<223> OTHER INFORMATION: Synthetic oligonucleotide primer

<400> SEQUENCE: 21
agttttgtgt atgcgttcaa taaccttt                               28

<210> SEQ ID NO 22
<211> LENGTH: 700
<212> TYPE: DNA
<213> ORGANISM: Artificial Sequence
<220> FEATURE:
<223> OTHER INFORMATION: pDrive/At39 promoter clone portion
<220> FEATURE:
<221> NAME/KEY: misc_feature
<222> LOCATION: 17, 436, 512, 579, 617, 619, 630, 699
<223> OTHER INFORMATION: n = A,T,C or G

<400> SEQUENCE: 22
ttgatctttt aattcgngat tgcacaagct tgcttataag ctactctttg ccaacaaact    60
cgcaacaatg atttctagaa ctatactcag ttgatggggg aagaaaatgt tgaaagttgt   120
acaatgaatc aagttaaagt taaaatactt ttttcccgat tctctgcagg ttacatatat   180

```
gtgtatatac acagtatgtg aatgatcaaa agaagattt aatatatcta agcatgcaga    240
caaaaaccta ttgctaaaaa gatttctaag aaccggagac cgtttaccaa acaaaatatg    300
aagttgaatt catcccattt gtcactcgat tagacaagat cgtcgaacg aagatatcta    360 ttaacgatct actaacttta gttaaatcgt gacaaaacac acatcattca tatttgatag    420
tgaataagtc ggtggnccat cgttttaact ttgattgata tccttaaaat tgatgcatag    480
ctttaaacaa ccaatacttt cttatggatt gnttttcttc caacttctct aagggtttta    540
ttttagaaaa ttgattataa gtattaaatg aaatctaana gaaaaaaaaa aaaaaaaga    600 ggagaaagat gtacaantnc ccatgccttn agattccgga ttacgtgtgt cactctttttt   660 atagctttaa cgcgatggtc cctcaaccgt gaaccgacnc    700
```

```
<210> SEQ ID NO 23
<211> LENGTH: 618
<212> TYPE: DNA
<213> ORGANISM: Arabidopsis thaliana
<220> FEATURE:
<221> NAME/KEY: misc_feature
<222> LOCATION: (380)..(380)
<223> OTHER INFORMATION: Inadvertent typographical deletion of 80
      nucleotides. Nucleotide 379 should be followed by 80 nucleotides
      identical to nucleotides 481-560 of SEQ ID NO: 22, except the
      nucleotide corresponding with nucleotide 516 of SEQ ID NO: 22,
      which is unidentified.

<400> SEQUENCE: 23
```

```
gcacaagctt gcttataagc tactctttgc aacaaattc gcaacaatga tttctagaac    60
tataatcagt tgatggggga agaaaatgtt gaaagttgta caatgaatca agttaaagtt    120
aaaatacttt ttccccgatt ctctgcaggt tacatatatg tgtatataca cagtatgtga    180
atgatcaaaa agaagattta atatatctaa gcatgcagac aaaaacctat tgctaaaaag    240
atttctaaga accggagacc gtttaccaaa caaaatatga agttgaattc atcccatttg    300
tcactcgatt agacaagatt cgtcgaacga agatatctat taacgatcta ctaactttag    360
ttaaatcgtg acaaaacacc tttaaacaac caatactttc ttatggattg ttttttcttcc    420 aacttctcta agggttttat tttagaaaat tgattataag tattaaatga atctaagag    480 aaaaaaaaaa aaaaaaagag gagaaagatg tagaagttcc catgccttta gattcggatt    540
acgtgtgtca ctcttttttat agctttaacg cgatggtcgc tcaacgtgaa cgacattgtc    600
ccactaagaa aaataatg    618
```

```
<210> SEQ ID NO 24
<211> LENGTH: 221
<212> TYPE: DNA
<213> ORGANISM: Artificial
<220> FEATURE:
<223> OTHER INFORMATION: pBI/At39 promoter clone portion
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t

<400> SEQUENCE: 24
```

```
cttttgcatt gtgtgaaacc ttcgagtttt ctcttcatct tctcaaagta acaaactttc    60
tccaaacaga ttattattaa aacaatctca tcaagaacta cgatgaaatt cccggctgta    120
aaagttcgga tccccgggta cggtcagtcc cttatgttac gtcctgtaga aaccccaacc    180
```

```
-continued cggaaatcaa aaaanagacg gcggggggcat aangggggga a                221

<210> SEQ ID NO 25
<211> LENGTH: 224
<212> TYPE: DNA
<213> ORGANISM: Arabidopsis thaliana

<400> SEQUENCE: 25
cttttgcatt gtgtgaaacc ttcgagtttt ctcttcatct tctcaaagta acaaactttc    60
tccaaacaga ttattattaa aacaatctca tcaagaacta cgatgtttaa gggccgacat   120
tttcaaggga tcccctattg ttacgtcctg tagaaacccc aacccgtgaa atcaaaaaac   180
tcgacggcct gtgggcattc agtctggatc gcgaaaactg tgga                   224
```